(12) United States Patent
Hattori et al.

(10) Patent No.: US 7,598,228 B2
(45) Date of Patent: Oct. 6, 2009

(54) THERAPEUTIC METHODS AND AGENTS FOR DISEASES ASSOCIATED WITH DECREASED EXPRESSION OF AOP-1 GENE OR AOP-1

(75) Inventors: Fumiyuki Hattori, Osaka (JP); Keijiro Sugimura, Osaka (JP); Mayumi Furuya, Osaka (JP)

(73) Assignee: Asubio Pharma Co., Ltd., Tokyo (JP)

( * ) Notice: Subject to any disclaimer, the term of this patent is extended or adjusted under 35 U.S.C. 154(b) by 90 days.

(21) Appl. No.: 10/642,272

(22) Filed: Aug. 18, 2003

(65) Prior Publication Data

US 2005/0277606 A1 Dec. 15, 2005

Related U.S. Application Data

(63) Continuation of application No. PCT/JP02/01358, filed on Feb. 18, 2001.

(30) Foreign Application Priority Data

Feb. 16, 2001 (JP) .............................. 2001-041003

(51) Int. Cl.
*A61K 48/00* (2006.01)
*A01N 63/00* (2006.01)

(52) U.S. Cl. ........................................ 514/44; 424/93.1

(58) Field of Classification Search .................. None
See application file for complete search history.

(56) References Cited

U.S. PATENT DOCUMENTS 6,034,250 A 3/2000 Goldstein et al.

FOREIGN PATENT DOCUMENTS

| EP | 503582 A1 | 9/1992 |
|---|---|---|
| EP | 515995 A2 | 12/1992 |
| EP | 768314 A1 | 4/1997 |
| WO | WO 95/04041 A1 | 2/1995 |
| WO | WO 99/53917 A1 | 10/1999 |
| WO | WO 00/55174 A1 | 9/2000 |

OTHER PUBLICATIONS

Hajjar, RJ et al. Circ Res 86:616-621, 2000.*
Adams, AK et al. Am Fam Physician 60(3):895-904, 1999.*
Hajjar, RJ et al. PNAS 95:5251-5256, 1998.*
del Monte, F et al. Circulation 104:1424-1429, 2001.*
Matsushima, S et al. Circulation 113:1779-1786, 2006.*
Chirmule, N et al. Gene Therapy 6:1574-1583, 1999.*
Sutherland FJ and DJ Hearse. Pharmacol Res 41(6):613-627, 2000.*
Skrzypiec-Spring, M et al. J Pharmacol Toxicol Methods 55:113-126, 2007.*
Kennell, DE. Progr Nucl Acid Res Mol Biol 11:259-301, 1971.*
Nemoto, Y et al. Gene 91(2):261-265, 1990; abstract only.*
Bryk, R. et al., "Peroxynitrite reductase activity of bacterial peroxiredosins", *Nature* (2000), vol. 407, No. 6801, pp. 211-215.
Matsumoto, Akio et al., "Cloning of the peroxiredoxin gene family in rats and characterization of the fourth member", *FEBS Letters* (1999), vol. 443, No. 3, pp. 246-250.
Nemoto, Y. et al., "Antisense RNA of the latent period gene (MER5) inhibits the differentiation of murine erythroleukemia cells", *Gene* (1990), vol. 91, No. 2, pp. 261-265.
Tsuji, K. et al., Mammalian antioxidant protein complements alkylhydroperoxide reductase (ahpC) mutation in *Escherichia coli.*, *Biochem. J.* (1995), vol. 307, No. Pt. 2, pp. 377-381.
Watabe, S. et al., "Purification and characterization of a substrate protein for mitochondrial ATP-dependent protease in bovine adrenal cortex", *J. Biochem.* (1994), vol. 115, No. 4, pp. 648-654.
Yamamoto, T. et al., "Cloning of a housekeeping-type gene (MER5) preferentially expressed in murine erythroleukemia cells", *Gene* (1989), vol. 80, No. 2, pp. 337-343.
Tatewaki, Masuo, "Ketsueki Kansaibo no Zoshoku to Bunka", *Chem. Abstr.* (1992), vol. 117, (Columbus, OH) [English translation of excerpts].
Tatewaki, Masuo, "Sekkekkyu Bunka no Yudo", *Chem. Abstr.* (1995), vol. 122, (Columbus, OH) [English translation of excerpts].

* cited by examiner

*Primary Examiner*—Deborah Crouch
*Assistant Examiner*—Marcia S Noble
(74) *Attorney, Agent, or Firm*—Hunton & Williams LLP

(57) ABSTRACT

A prophylactic or therapeutic method for a disease associated with decreased expression of AOP-1 gene or AOP-1, comprising (1) transfecting a nucleic acid encoding AOP-1 or a nucleic acid encoding a polypeptide having an addition, deletion or substitution of one or more amino acids as compared with the amino acid sequence of AOP-1 while retaining the function of AOP-1, or (2) administering a material enhancing the expression of AOP-1 gene, a material enhancing the production of AOP-1 or a material enhancing the function of AOP-1.

5 Claims, 23 Drawing Sheets

A: Sham normal gromeruli and proximal tubules
B: Vehicle
C: AOP-1
×200, PAS stained ◯ glomeruli

*: proliferation of mesangial cells

☐ Atrophy of proximal and distal tubules enlarged image 1 (gromeruli)

A-1: Sham

B-1: Vehicle

C-1: AOP-1 enlarged image 2 (renal tubules)

normal (AOP-1)

atrophic (Vehicle)

THERAPEUTIC METHODS AND AGENTS FOR DISEASES ASSOCIATED WITH DECREASED EXPRESSION OF AOP-1 GENE OR AOP-1

This application is a continuation application of International Application No. PCT/JP02/01358, filed Feb. 18, 2002, which claims benefit of priority of Japanese Application No. 41003/2001, filed Feb. 16, 2001.

FIELD OF INVENTION

The present invention relates to methods for preventing, treating or diagnosing diseases, prophylactic or therapeutic agents for diseases, methods for screening materials suitable as active ingredients of pharmaceutical preparations, non-human transgenic animals, and transformed tissues, etc.

BACKGROUND OF INVENTION

In many diseases, compensatory changes occur in tissue cells with the progress of pathology to achieve a temporary equilibrium. In the process of further aggravation of pathology, the compensatory mechanism breaks down leading to cellular dysfunction and finally cellular death. This cellular dropout makes it more difficult to cure diseases and invites unfavorable prognosis or recurrence. Especially in the therapy of diseases in non-regenerative organs such as heart, brain and kidney, it is important to suppress cellular necrosis/dropout.

(1) Heart Diseases a. Heart Failure: Heart failure is defined as a condition in which the heart cannot maintain an adequate cardiac output to various organs due to reduced myocardial contractility. As a preliminary stage to heart failure, compensatory remodeling occurs in the heart for the purpose of maintaining normal systemic circulation. At this stage, cardiac myocytes continuously enlarge and grow to maintain a high cardiac pumping pressure as well as cardiac output; but at the same time fibrosing in cardiac tissue advances to increase a load imposed on contracted cells. When the balance between the load on cardiac myocytes and compensation by enlargement reaches a limit, heart function breaks down leading to heart failure. It is known that contractility is lowered in cardiac myocytes under heart failure condition (Am J Physiol 1997 Vol. 273(1 Pt 2), H183-91). Conventional therapies for chronic heart failure involve administering cardiac stimulants that increase myocardial contractility such as digitalis and xanthine drugs after a patient falls into heart failure condition or fails to be able to lead a normal daily life. However, these drugs have been shown to promote cellular death, and to cause a deterioration in survival rates due to overconsumption of myocardial energy during prolonged administration. Recently, therapies with β-blockers and ACE inhibitors have been prevailing that reduce overload on the heart by the inhibition of the sympathetic nervous system and the inhibition of the renin-angiotensin system, respectively, that are activated at the compensatory remodeling stage. However, these drugs are less effective for patients who already have a heart failure condition, but rather act prophylactically against chronic heart failure because they have an action of mechanism based on preventing enlargement of cardiac myocytes. Moreover, the fact that long-term survival rates of patients with chronic heart failure have not fully improved even after these drugs came to the market suggests a limit to the action of mechanism of these drugs. Therefore, there is an urgent need for development of a novel therapeutic agent for chronic heart failure that is able to improve both quality of life and survival rates at the chronic heart failure stage after breakdown at the compensatory stage. It would be desirable to develop a novel drug for treating cellular death and cellular dysfunction, which are essential causes of the breakdown mechanism associated with the transition from the compensatory stage to the failure stage.

b. Ischemic Heart Diseases: Ischemic heart diseases are characterized by coronary flow failure including angina pectoris and myocardial infarction. For example, angina pectoris is classified into angina pectoris decubitus and angina pectoris of effort. Currently, serious cases are surgically treated to physically dilate vessels and then place a stent or the like. Relatively mild cases are treated with vasodepressors for treating an attack such as nitrates, nitroglycerin and nicorandil. Cholesterol reducers and anticoagulant agents are formulated for the purpose of preventing infarction. Thus, therapies for acute stage or improving blood circulation are being established. Attack is thought to result from the lowered myocardial adaptability due to the accumulation of injuries caused by chronic ischemia at the subclinical stage. However, no therapy has been established for this phase at present. It would also be desirable to prevent massive ischemia from the onset of angina because many cases show transition from angina to severe myocardial infarction, but a therapy suitable for this phase has not been found yet, either.

(2) Neurodegenerative Diseases

Neurodegenerative diseases are characterized by neuronal degeneration, and specifically include injuries of the white matter such as cerebral infarction, Alzheimer's disease, Parkinson's disease, brain trauma, Huntington's chorea, cerebrovascular dementia, motor neuron degeneration and Binswanger's disease. An excessive increase of the extracellular level of a neurotransmitter glutamate has been commonly found in cerebral infarction, cerebrovascular dementia, brain trauma, Alzheimer's disease, motor neuron degeneration, Parkinson's disease, etc. (Eur J Neurosci 2000 Vol. 12(8), 2735-45; Brain Res 1994 Vol. 11, No. 642(1-2), 117-122; Acta Neurochir Suppl. 2000 Vol. 76, 437-8; Neurosci Lett 2001 Vol. 299(1-2), 37-40; J Neurosci Res 2001 Vol. 63(5), 377-87; Drugs Aging 2001 Vol. 18(10), 717-24). This excessive glutamate stimulates glutamate receptors (NMDA receptors) on the surfaces of neurons to induce excessive neural excitation. It is widely accepted that this excessive neural excitation induces breakdown of intracellular ionic environments to cause cellular death. Currently used therapeutic agents for cerebral infarction such as antiplatelet drugs and thrombolytic agents are intended to reopen and maintain blood flow, but any therapy having a protective effect on neurons themselves has not been established. NMDA receptor antagonists, glutamate release inhibitors and active oxygen scavengers are being developed as therapeutic agents at a testing stage, but have not been verified for their efficacy. Choline esterase inhibitors were recently approved as therapeutic agents for Alzheimer's disease, but they have a mechanism based on improving learning function by promoting intercellular signal transduction rather than directly suppressing neuronal death. It would be desirable to develop a therapeutic agent having an action mechanism based on neuronal protection as an effective therapy for a series of neurodegenerative diseases.

(3) Rheumatism

Among rheumatic diseases, rheumatoid arthritis is chronic arthritis characterized by continuous proliferation of articular synovial membranes and said to be caused by autoimmunization. It is thought that aging and hereditary predisposition are combined with environmental factors to form complex risk factors inducing immunization against autoantigens after some articular inflammation such as infectious diseases. In advanced rheumatoid arthritis, not only cartilage destruction and bone destruction but also chondroblast death and osteoblast death have been reported (Arthritis Rheum 1999 Vol. 42(7), 1528-37; Z Rheumatol 2000 Vol. 59, Suppl. 1, 10-20). The disease seems to enter into an irreversible stage upon chondroblast and osteoblast death. Current therapies are based on immunosuppression using steroid or non-steroid drugs, but their therapeutic effects are neither sustained nor radical. Thus, it would be desirable to develop a novel therapeutic agent having a mechanism based on the protection of joints, osteoblasts and chondroblasts.

(4) Renal Diseases

Among renal diseases, chronic renal failure is characterized by injury to glomeruli and renal tubules in the kidney, and specifically includes diabetic nephropathy, hypertensive nephropathy, lupus nephropathy, etc. Abnormal functions in glomeruli serving to filter waste products in blood, and in renal tubules serving to reabsorb filtrate from urine, result from cellular injury caused by glycoproteins derived from hyperglycemia, cellular injury by hypertensive circulation failure and autoimmune chronic nephritis. An effective therapy for chronic renal failure has not been found at present, and symptomatic therapies are applied such as steroid or non-steroid drugs for inflammation such as lupus nephritis and antihypertensives for hypertensive renal failure. It would be desirable at present to provide a drug directly acting on glomerular cells and tubular cells to protect them.

(5) Hepatic Diseases

Hepatic diseases progress to cirrhosis and hepatic failure via viral, alcoholic and drug-induced hepatitis. Symptomatic therapies therefor include ursodeoxycholic acid, glycyrrhizin drugs and herbal medicine. Interferon therapy is a causal therapy for viral hepatitis, but has strong side effects and insufficient therapeutic effect. It can be said that hepatic failure such as cirrhosis is caused by chronic overstress on the liver, which is originally a regenerative organ but fails to regenerate hepatic function. Thus, protection of hepatic cells may be clearly effective for preventing hepatic failure. However, an effective therapy with few side effects has not been found at present.

On the other hand, AOP-1 gene was identified as a factor whose expression level increases when mouse erythroleukemia cells are induced by DMSO to differentiate (Gene 1989 Vol. 80, 337-343: initially named MER-5, and later AOP-1). Subsequently, AOP-1 protein was found to belong to the peroxiredoxin family and became to be commonly called peroxiredoxin 3 (PRx3) in the literature (AOP-1 protein is hereinafter referred to as AOP-1). The peroxiredoxin family is a class of proteins characterized by thiol-specific antioxidant activity by biochemical analysis using purified proteins (Proc. Natl. Acad. Sci. USA 1994 Vol. 91, 7017-7021) and widely conserved from prokaryotes to higher organisms including human. Recently, analysis using bacterial peroxiredoxin showed that peroxiredoxins are capable of scavenging peroxynitrite (Nature 2000 vol. 407, No. 14, 211). In the peroxiredoxin family, AOP-1 is distinguished from other peroxiredoxins in that it is localized in mitochondria (Methods in enzymology, vol. 300). Superoxide dismutase (SOD) and catalase that are widely known as antioxidant proteins do not demand the thiol group for producing antioxidant activity and they cannot scavenge peroxynitrite, so that the peroxiredoxin family is also expected to differ in physiological functions from SOD and catalase. Recently, protective effect against hydrogen peroxide injury in cultured thyroid cells was found as a physiological function of peroxiredoxin type 1 and type 2 localized in the cytoplasm (J. Biological Chemistry 2000 Vol. 275, No. 24, 18266-18270), but a physiological function of AOP-1 (peroxiredoxin type 3) localized in mitochondria has not been found. The direct relation of the peroxiredoxin family including AOP-1 to any disease has not been shown, either.

The present invention aims to provide a method for preventing, treating or diagnosing diseases associated with decreased expression of AOP-1 gene or AOP-1 such as heart diseases (chronic heart failure, ischemic heart failure, ischemic heart diseases, etc.), neurodegenerative diseases (cerebral infarction, Alzheimer's disease, Parkinson's disease, brain trauma, Huntington's chorea, cerebrovascular dementia, motor neuron degeneration, Binswanger's disease, etc.), rheumatism (rheumatoid arthritis, etc.), renal diseases (renal failure, etc.), hepatic diseases (hepatitis, cirrhosis, hepatic failure, etc.), a prophylactic or therapeutic drug for these diseases, a method for screening a material suitable as an active ingredient of said drug, a non-human transgenic animal and transformed tissue in which the expression of AOP-1 gene is suppressed or deleted, etc.

SUMMARY OF INVENTION

The present invention relates to:

(1) a prophylactic or therapeutic method for a disease associated with decreased expression of AOP-1 gene or AOP-1, comprising (1) transfecting a nucleic acid encoding AOP-1 or a nucleic acid encoding a polypeptide having an addition, deletion or substitution of one or more amino acids as compared with the amino acid sequence of AOP-1 while retaining the function of AOP-1, or (2) administering a material enhancing the expression of AOP-1 gene, a material enhancing the production of AOP-1 or a material enhancing the function of AOP-1, or (3) administering AOP-1 protein or a polypeptide having an addition, deletion or substitution of one or more amino acids as compared with the amino acid sequence of AOP-1 while retaining the function of AOP-1; as used herein, AOP-1 gene means AOP-1 mRNA unless otherwise specified though AOP-1 gene usually means to contain nucleic acid sequences encoding AOP-1 (exon sequences) and intervening nucleic acid sequences (intron sequences) and nucleic acid sequences regulating the transcription of AOP-1 gene;

(2) the prophylactic or therapeutic method as defined in (1) above comprising transfecting a nucleic acid for AOP-1 gene or a nucleic acid encoding a polypeptide having an addition, deletion or substitution of one or more amino acids as compared with the amino acid sequence of AOP-1 while retaining the function of AOP-1 into cells of an affected tissue;

(3) the prophylactic or therapeutic method as defined in (1) above comprising administering a material enhancing the expression of AOP-1 gene;

(4) the prophylactic or therapeutic method as defined in (1) above comprising administering a material enhancing the production of AOP-1;

(5) the prophylactic or therapeutic method as defined in (4) above wherein the material enhancing the production of AOP-1 is a nucleic acid encoding AOP-1 or a nucleic acid encoding a polypeptide having an addition, deletion or substitution of one or more amino acids as compared with the amino acid sequence of AOP-1 while retaining the function of AOP-1;

(6) the prophylactic or therapeutic method as defined in (1) above comprising administering a material enhancing the function of AOP-1;

(7) the prophylactic or therapeutic method as defined in any one of (1) to (6) above wherein the disease associated with decreased expression of AOP-1 gene or AOP-1 is chronic heart failure, ischemic heart failure, ischemic heart disease, rheumatoid arthritis, neurodegenerative disease, hepatic disease or renal failure;

(8) a prophylactic or therapeutic agent for a disease associated with decreased expression of AOP-1 gene or AOP-1, comprising as an active ingredient (1) a nucleic acid encoding AOP-1 or a nucleic acid encoding a polypeptide having an addition, deletion or substitution of one or more amino acids as compared with the amino acid sequence of AOP-1 while retaining the function of AOP-1, or (2) a material enhancing the expression of AOP-1 gene, a material enhancing the production of AOP-1 or a material enhancing the function of AOP-1, or (3) AOP-1 protein or a polypeptide having an addition, deletion or substitution of one or more amino acids as compared with the amino acid sequence of AOP-1 while retaining the function of AOP-1;

(9) the prophylactic or therapeutic agent as defined in (8) above comprising as an active ingredient a nucleic acid for AOP-1 gene or a nucleic acid encoding a polypeptide having an addition, deletion or substitution of one or more amino acids as compared with the amino acid sequence of AOP-1 while retaining the function of AOP-1;

(10) the prophylactic or therapeutic agent as defined in (8) above comprising as an active ingredient a material enhancing the expression of AOP-1 gene;

(11) the prophylactic or therapeutic agent as defined in (8) above comprising as an active ingredient a material enhancing the production of AOP-1;

(12) the prophylactic or therapeutic agent as defined in (11) above wherein the material enhancing the production of AOP-1 is a nucleic acid encoding AOP-1 or a nucleic acid encoding a polypeptide having an addition, deletion or substitution of one or more amino acids as compared with the amino acid sequence of AOP-1 while retaining the function of AOP-1;

(13) the prophylactic or therapeutic agent as defined in (8) above comprising as an active ingredient a material enhancing the function of AOP-1;

(14) the prophylactic or therapeutic agent as defined in any one of (8) to (13) above wherein the disease associated with decreased expression of AOP-1 gene or AOP-1 is chronic heart failure, ischemic heart failure, ischemic heart disease, rheumatoid arthritis, neurodegenerative disease, hepatic disease or renal failure;

(15) a diagnostic method for a disease associated with decreased expression of AOP-1 gene or AOP-1, comprising determining the expression level of AOP-1 gene or the production level of AOP-1 to make a diagnosis based on the expression level or production level;

(16) the diagnostic method as defined in (15) above wherein the disease associated with decreased expression of AOP-1 gene or AOP-1 is chronic heart failure, ischemic heart failure, ischemic heart disease, rheumatoid arthritis, neurodegenerative disease, hepatic disease or renal failure;

(17) a diagnostic agent or diagnostic kit for a disease associated with decreased expression of AOP-1 gene or AOP-1, comprising a means for determining the expression level of AOP-1 gene or the production level of AOP-1 as a measure;

(18) the diagnostic agent or diagnostic kit as defined in (17) above wherein the disease associated with decreased expression of AOP-1 gene or AOP-1 is chronic heart failure, ischemic heart failure, ischemic heart disease, rheumatoid arthritis, neurodegenerative disease, hepatic disease or renal failure;

(19) a non-human transgenic animal suitable for use as a pathologic model of a disease associated with decreased expression of AOP-1 gene or AOP-1 wherein the production of AOP-1 is suppressed or the expression of AOP-1 gene is suppressed or AOP-1 gene is deleted;

(20) the non-human transgenic animal as defined in claim 19 wherein the disease associated with decreased expression of AOP-1 gene or AOP-1 is chronic heart failure, ischemic heart failure, ischemic heart disease, rheumatoid arthritis, neurodegenerative disease, hepatic disease or renal failure;

(21) a transformed tissue or transformed cell suitable for use as a tissue model or a cell model of a disease associated with decreased expression of AOP-1 gene or AOP-1 wherein the production of AOP-1 is suppressed or the expression of AOP-1 gene is suppressed or AOP-1 gene is deleted;

(22) the transformed tissue or transformed cell as defined in (21) above wherein the disease associated with decreased expression of AOP-1 gene or AOP-1 is chronic heart failure, ischemic heart failure, ischemic heart disease, rheumatoid arthritis, neurodegenerative disease, hepatic disease or renal failure;

(23) a method for screening at least one selected from the group consisting of a material enhancing the expression of AOP-1 gene, a material enhancing the production of AOP-1 or a material enhancing the function of AOP-1, comprising administering or adding a synthesized or genetically engineered material or a natural material or a derivative thereof to the non-human transgenic animal or transformed tissue or transformed cell as defined in any one of (18) to (21) above to detect the expression level of AOP-1 gene or the production level of AOP-1;

(24) a method for screening at least one selected from the group consisting of a material enhancing the expression of AOP-1 gene, a material enhancing the production of AOP-1 or a material enhancing the function of AOP-1, comprising contacting a synthesized or genetically engineered material or a natural material or a derivative thereof with (1) a transformed cell or an in vitro expression system having a transcriptional regulatory region of AOP-1 gene and AOP-1 gene or a reporter gene to detect the expression level of AOP-1 gene or the reporter gene or with (2) AOP-1 or a target molecule of AOP-1 to detect the amount of AOP-1 or the target molecule of AOP-1;

(25) the screening method as defined in (24) above comprising constructing an expression vector having a transcriptional regulatory region of AOP-1 gene linked upstream or downstream of the translation region of a reporter gene, then culturing a suitable host cell transfected with said vector, adding a synthesized or genetically engineered material or a natural material or a derivative thereof to the cultured cell and detecting changes in the expression level of the reporter gene or the production level of the reporter protein after a given period;

(26) the screening method as defined in (24) above comprising contacting a synthesized or genetically engineered material or a natural material or a derivative thereof with AOP-1 or a target molecule of AOP-1 to detect the amount of AOP-1 or the target molecule of AOP-1 bound or unbound to said material;

(27) the screening method as defined in (24) above comprising immobilizing AOP-1 or a target molecule of AOP-1 on a substrate and adding a synthesized or genetically engineered material or a natural material or a derivative thereof and AOP-1 or target molecule of AOP-1 to the immobilized AOP-1 or target molecule of AOP-1 to detect the amount of AOP-1 or the target molecule of AOP-1 bound or unbound;

(28) the screening method as defined in (24) above comprising immobilizing a synthesized or genetically engineered material or a natural material or a derivative thereof on a substrate and adding AOP-1 or a target molecule of AOP-1 to the immobilized material to detect the amount of AOP-1 or the target molecule of AOP-1 bound or unbound;

(29) a method for screening a material enhancing the function of AOP-1, comprising contacting a synthesized or genetically engineered material or a natural material or a derivative thereof with AOP-1 or a target molecule of AOP-1 to determine the antioxidant or peroxynitrite scavenging activity of AOP-1;

(30) the screening method as defined in (29) above comprising adding a synthesized or genetically engineered material or a natural material or a derivative thereof and AOP-1 or a target molecule of AOP-1 to AOP-1 or the target molecule of AOP-1 to determine the antioxidant or peroxynitrite scavenging activity of AOP-1;

(31) the screening method as defined in (29) above comprising immobilizing AOP-1 or a target molecule of AOP-1 on a substrate and adding a synthesized or genetically engineered material or a natural material or a derivative thereof and AOP-1 or the target molecule of AOP-1 to the immobilized AOP-1 or target molecule of AOP-1 to determine the antioxidant or peroxynitrite scavenging activity of AOP-1;

(32) the screening method as defined in (29) above comprising immobilizing a synthesized or genetically engineered material or a natural material or a derivative thereof on a substrate and adding AOP-1 or a target molecule of AOP-1 to the immobilized material to determine the antioxidant or peroxynitrite scavenging activity of AOP-1;

(33) a use of (1) a nucleic acid for AOP-1 gene or a nucleic acid encoding a polypeptide having an addition, deletion or substitution of one or more amino acids as compared with the amino acid sequence of AOP-1 while retaining the function of AOP-1, or (2) a material enhancing the expression of AOP-1 gene, a material enhancing the production of AOP-1 or a material enhancing the function of AOP-1, or (3) AOP-1 protein or a polypeptide having an addition, deletion or substitution of one or more amino acids as compared with the amino acid sequence of AOP-1 while retaining the function of AOP-1, for the preparation of a prophylactic or therapeutic method for a disease associated with decreased expression of AOP-1 gene or AOP-1;

(34) the use as defined in (33) above comprising as an active ingredient a nucleic acid for AOP-1 gene or a nucleic acid encoding a polypeptide having an addition, deletion or substitution of one or more amino acids as compared with the amino acid sequence of AOP-1 while retaining the function of AOP-1;

(35) the use as defined in (33) above comprising as an active ingredient a material enhancing the expression of AOP-1 gene;

(36) the use as defined in (35) above wherein the material enhancing the production of AOP-1 is a nucleic acid encoding AOP-1 or a nucleic acid encoding a polypeptide having an addition, deletion or substitution of one or more amino acids as compared with the amino acid sequence of AOP-1 while retaining the function of AOP-1;

(37) the use as defined in (33) above comprising as an active ingredient a material enhancing the production of AOP-1;

(38) the use as defined in (33) above comprising as an active ingredient a material enhancing the function of AOP-1; and

(39) the use as defined in any one of (33) to (38) above wherein the disease associated with decreased expression of AOP-1 gene or AOP-1 is chronic heart failure, ischemic heart failure, ischemic heart disease, rheumatoid arthritis, neurodegenerative disease, hepatic disease or renal failure.

BRIEF DESCRIPTION OF FIGURES

FIG. 8.

FIG. 12.

FIG. 13.

FIG. 14.

FIG. 15.

DETAILED DESCRIPTION OF PREFERRED EMBODIMENTS

Figure 1:
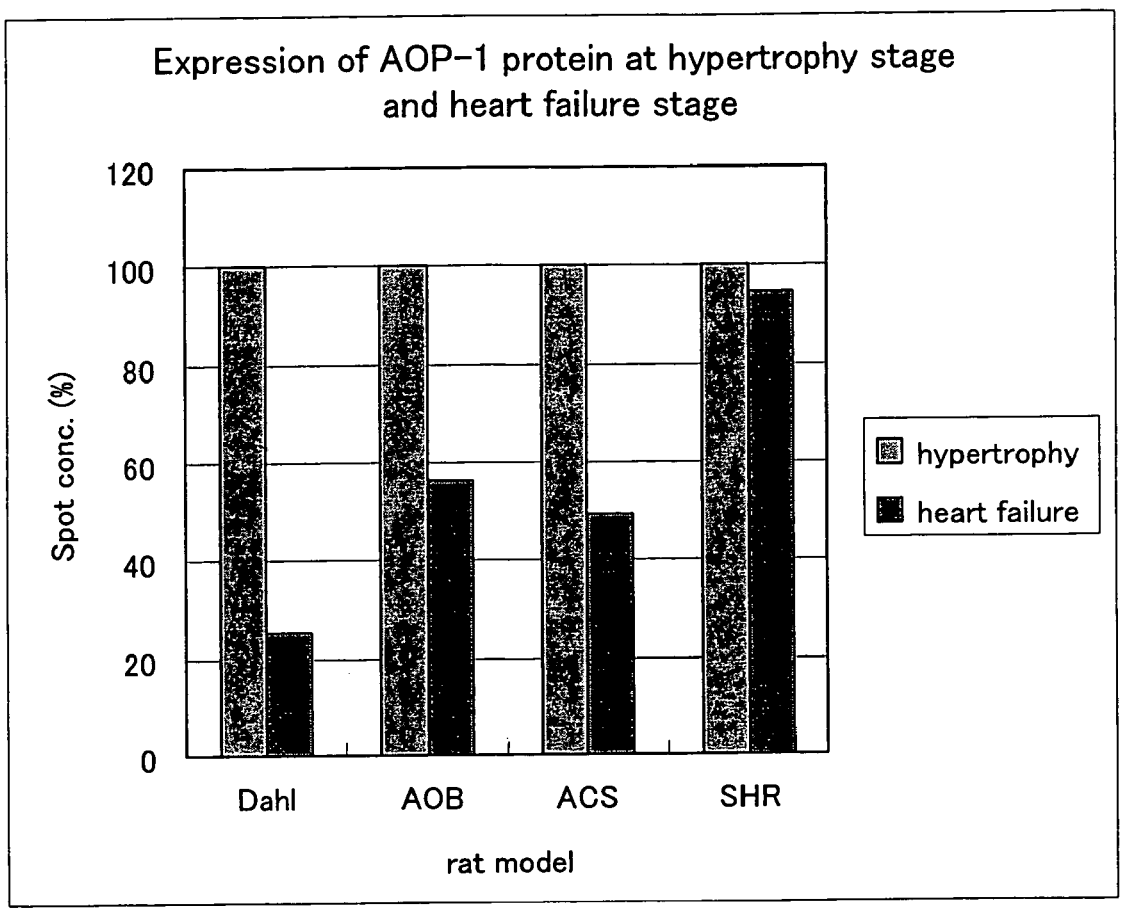
FIG. 1 shows changes in the expression of AOP-1 protein at cardiac hypertrophy stage and heart failure stage in various pathologic model rats of chronic heart failure.

As used herein, "function of AOP-1" refers to the effect of activating/protecting organs and cells such as metabolic activation of heart/myocytes, protection of functions of heart/ myocytes, suppression of heart/myocardial cellular death, activation of neurons, suppression of neuronal death and protection of renal function. Thus, the expression "having the function of AOP-1" as used herein means having the effect of activating/protecting organs and cells. Whether or not a material "has the function of AOP-1" is determined by various methods described in the section (6) Screening methods and in the examples below.

As used herein, "heart disease" means heart failure (including chronic heart failure, ischemic heart failure, diabetic heart failure, etc.), ischemic heart disease (including angina, myocardial infarction, etc.), etc. As used herein, "neurodegenerative disease" means cerebral infarction, Alzheimer's disease, Parkinson's disease, brain trauma, Huntington's chorea, cerebrovascular dementia, motor neuron degeneration, Binswanger's disease, etc. As used herein, "rheumatism" includes chronic rheumatoid arthritis, etc. As used herein, "renal disease" means renal failure such as diabetic nephropathy, hypertensive nephropathy, lupus nephropathy, etc. As used herein, "hepatic disease" means hepatitis (including viral hepatitis, alcoholic hepatitis and drug-induced hepatitis), cirrhosis, hepatic failure, etc.

We performed a series of experiments in order to find common causes of inducing cellular dysfunction or cellular death which is a common phenomenon in heart disease, neurodegenerative disease, rheumatism, renal disease and hepatic disease.

(1) Heart Diseases

In order to investigate the cause of breakdown at the compensatory stage in chronic heart failure, changes in the expression of various proteins in tissues with the progress from heart hypertrophy to chronic heart failure were first determined. A mixed protein solution in tissue extracts was separated into crude fractions consisting of a water-soluble fraction and a surfactant-soluble fraction, each of which was then analyzed by two-dimensional electrophoresis. Aortostenotic rats (heart pressure overload model), arteriovenous shunt rats (heart volume overload model), hereditary hypertensive rats (SHR) and Dahl salt-sensitive rats were used as pathologic models of chronic heart failure for comparative analysis. The proteins varying in the expression level with breakdown at the compensatory stage commonly in many models were searched to find common proteins related to chronic heart failure. Among them, AOP-1 protein was found to be decreased in expression with breakdown at the compensatory stage.

Gene expression analysis was performed to study whether or not changes in said protein with the progress of chronic heart failure result from any regulation at the level of gene expression. As a result, all the models tested showed suppressed expression of the gene, indicating that the decrease of AOP-1 with the progress of chronic heart failure results from the regulation of gene expression. Gene expression analysis using heart failure rats following myocardial infarction as an ischemic chronic heart failure model also showed suppressed expression of the gene. Thus, decreased expression of AOP-1 gene and therefore a decrease of AOP-1 was commonly found in chronic heart failure of a wide variety of causes. Analysis of changes in the gene expression of type 2 peroxiredoxin thiol-specific antioxidant (TSA) and the expression of CuZn-superoxide dismutase (CuZn-SOD), Mn-superoxide dismutase (Mn-SOD) and catalase genes having common antioxidant activity showed no change in the gene expression level of TSA, CuZn-SOD, Mn-SOD and catalase. Thus, AOP-1 was found to characteristically decrease expression with the transition to the heart failure stage among typical antioxidant proteins in the peroxiredoxin family. This shows that AOP-1 gene undergoes a different gene regulation from other antioxidant proteins.

Then, we tested whether or not AOP-1 has some effect on the improvement or aggravation of heart function. We began by isolating the full-length gene of rat AOP-1 gene to construct a suitable expression vector, and then transfected the AOP-1 gene into cultured rat cardiac myocytes. AOP-1 gene-transfected group was tested under the following experimental conditions: cells were cultured without oxygen (hypoxia), or cultured under hypoxia followed by reperfusion for a period (reperfusion), or cultured under normal oxia (untreated). In view of the influence of forced gene expression and protein production, control group transfected with E. coli β-galactosidase gene, which does neither harm nor good, was tested in parallel and comparative analyses were performed between both groups. Comparative method 1 involves counting the number of viable cells, comparative method 2 involves counting the number of autonomously pulsating cells among viable cells, and comparative method 3 involves confirming the number of viable cells and cellular metabolic activity according to the MTT assay (J. Immunol. Methods 1983 Vol. 65, 55-63). These three comparative analyses showed that the number of viable cells under hypoxia and reperfusion as well as the number of autonomously pulsating cells significantly increased in the AOP-1 gene transfected group as compared with the control group. In the MTT assay, the AOP-1 gene transfected group showed high levels under hypoxia, reperfusion and normal oxia as compared with the control group, indicating an increase in the number of viable cells during injury and an increase in metabolic activity during injury and normal states. Thus, it was found that AOP-1 shows high efficacy in both cell viability and cell function maintenance against hypoxic injury and reperfusion injury. We further constructed an adenovirus vector for expressing antisense AOP-1 (antisense AOP-1 vector) designed to express a complementary strand to AOP-1 gene. Generally, it has been reported that the mRNA expressed from this type of vector complementarily binds to mRNA expressed from endogenous AOP-1 gene to inhibit translation into a protein (Gene 1990 Vol. 91, 261-265). We cultured cardiac myocytes transfected with antisense AOP-1 vector, AOP-1 expression vector and β-galactosidase expression vector for 3 days in parallel with untransfected cells. The MTT assay was performed on each group to reveal that chromogenesis was suppressed in cells transfected with antisense AOP-1 vector and the number of viable cells macroscopically decreased. Thus, the suppressed expression of the endogenous AOP-1 by antisense AOP-1 vector adversely affected cell viability. In order to further directly compare the efficacy of AOP-1, TSA and CuZn-SOD in cellular protection effect, we constructed adenovirus vectors capable of forced expression of these genes. These vectors were transfected into rat cardiac myocytes to increase the respective proteins and the resistance to the following stresses was analyzed. As a result, AOP-1 showed the most effective cellular protective effect against stresses of hydrogen peroxide, hypoxia and high glucose. This suggests that AOP-1 plays an especially important role in the cell maintenance mechanism. The finding of a cellular protective effect on high glucose injury suggests that AOP-1 may be effective for diabetic heart diseases (diabetes-induced heart failure and ischemic heart disease (angina, myocardial infarction, etc.)).

These results show that the decrease of AOP-1 in various heart diseases is a major cause of breakdown of compensatory mechanism (pathologic aggravation).

It should be especially noted that AOP-1 can protect against not only active oxygen-induced injury during reperfusion but also various hypoxic injuries such as energy depletion injury and intracellular oxygenation injury and that it even activated cellular metabolic function under normal oxia. Thus, it was strongly suggested that the cellular function protective effect and cellular death suppression effect of AOP-1 are based on not only antioxidant activity but also a new function including cellular metabolic activation (mitochondrial activation). This new function of AOP-1 (i.e., mitochondrial activation) has never been found in any other antioxidant proteins. Thus, this is a novel and specific function of AOP-1.

We further injected AOP-1 gene into the heart and performed the following analyses with the purpose of testing whether or not AOP-1 shows a protective effect in vivo. As soon as the protein was expressed after the gene was injected, the heart was rapidly isolated and connected to a perfusion device. The isolation-induced injury was controlled by perfusing the heart with a solution containing a gas in an amount equivalent to that of blood to try to maintain heart function under conditions as found in vivo. Perfusion was temporarily stopped to turn this heart into an ischemic state and then resumed to study the influence of reperfusion. In the heart with forced expression of AOP-1, ischemic rigidity during ischemia was significantly retarded and a significantly better functional recovery was shown during reperfusion as well as a significant cellular necrosis suppressing effect during reperfusion as compared with the negative control heart (sham). Ischemic rigidity is shown to highly correlate to ATP depletion in cardiac myocytes (J Mol Cell Cardiol 1996, Vol. 28, 1045-1057). The AOP-1 mediated prolongation of the time from ischemia to ischemic rigidity shows that the mitochodrial activation of AOP-1 found by us in cultured cardiac myocytes also works in vivo in the heart. This result showed that AOP-1 protects against both ischemic injury and reperfusion injury not only in cultured cells but also in vivo via novel mitochondrial activation in addition to antioxidation. Thus, it was shown that transfection of AOP-1 gene or administration of a material enhancing the expression of AOP-1 or the function of AOP-1 provides effective therapy for ischemic heart failure and ischemic heart disease. As hypertrophy-induced circulation failure in the myocardial tissue is reported in not only ischemic heart failure and ischemic heart disease but also chronic heart failure (Chin. Med. Sci. J. 1995 Vol. 10(3), 151-157), ischemia and ischemic reperfusion seem to be common causes of injury in pathologies of chronic heart failure. Therefore, administration of the protein to the pathologic heart showing chronic heart failure or a sign of chronic heart failure is expected to be an effective therapy for chronic heart failure by protecting against myocardial cellular death and keeping the heart pulsating function.

(2) Affected Organs other than Heart

Then, gene expression analysis was performed in other affected organs for the purpose of investigating whether or not the function of AOP-1 is responsible for pathogenesis in organs other than heart. The result showed that the expression of AOP-1 also decreases in the kidney of a nephritis model, the brain in a neurodegenerative disease model, and the liver in an infectious hepatitis (septic shock) model. This strongly suggested that decreased expression of AOP-1 commonly contributes to pathogenesis/aggravation in many diseases. AOP-1 gene showed decreased expression in not only the heart failure model but also the brain tissue of the neurodegenerative disease model in contrast to CuZn-SOD and catalase genes which showed no change in expression. This demonstrated that the expression of AOP-1 gene also undergoes a different regulation from other antioxidant proteins in diseases of organs other than heart.

a. Neurodegenerative Diseases

An increase of the extracellular glutamate level induces excessive activation of glutamate receptors (NMDA receptors) in cerebral infarction, cerebrovascular dementia, brain trauma, Alzheimer's disease, motor neuron degeneration, Parkinson's disease, etc. (Eur J Neurosci 2000 Vol. 12(8), 2735-45; Brain Res 1994 Vol. 11, No. 642(1-2), 117-122; Acta Neurochir Suppl. 2000 Vol. 76, 437-8; Neurosci Lett 2001 Vol. 299(1-2), 37-40;J Neurosci Res 2001 Vol. 63(5), 377-87; Drugs Aging 2001 Vol. 18(10), 717-24). Cells stimulated by the activation of NMDA receptors open their calcium channels to lead to influx of calcium into the cells. Excessive activation of NMDA receptors induces calcium overload in cells. This calcium overload results in apoptosis or necrosis of neurons, whereby nervous function disorder becomes irreversible. Administration of AOP-1 may also be effective for cerebral nerve degeneration because they are also associated with decreased expression of AOP-1 as already shown. When AOP-1 was actually tested for the protection of glutamate injury in cultured neurons, cellular death was significantly suppressed in cells transfected with AOP-1 gene. It was also shown that neurite outgrowth is promoted and neuronal network formation is activated under unloaded condition. This may be due to the metabolic activation (novel function of AOP-1) caused by the overproduction of AOP-1. Thus, AOP-1 was found to be very useful in cell protection against calcium overload and neuronal activation in neurons.

To verify efficacy in neurodegenerative disease animal models, analyses were performed on an ibotenic acid-induced brain damage model. Ibotenic acid is an NMDA receptor agonist, which induces excessive intracellular calcium influx to lead to neuronal death. After an AOP-1 expression gene was injected into the brain's hippocampus to induce the expression of AOP-1, ibotenic acid was injected into the same site. After 2 days, the brain was removed and neurons were observed. As compared with a control group untransfected with AOP-1 gene, neuronal death was clearly suppressed in the brain transfected with AOP-1 gene. Quantitative analysis of the proliferation/infiltration of glial cells showed higher suppression as compared with the control group. As the proliferation/infiltration of glial cells has been shown to correlate with the amount of neuronal death (Journal of Neuroimmunology 2000 Vol. 1009, 105-111; Brain Research 1991, Vol. 565, 312-320), this result shows that neurons were protected by the transfection of AOP-1 gene. Thus, AOP-1 was found to also have a protective effect on neurons in the tissue. Therefore, administration of AOP-1 may be effective for neurodegenerative diseases such as cerebral infarction, cerebrovascular dementia, brain trauma, Alzheimer's disease, motor neuron degeneration, Parkinson's disease, etc.

b. Renal Diseases

Administration of AOP-1 may be effective for renal diseases as well as heart diseases and neurodegenerative diseases because the renal failure model also showed decreased expression of AOP-1 as shown above. To verify the efficacy of AOP-1 gene against chronic renal failure, analysis was actually performed on a Thy-1 nephritis model. The Thy-1 nephritis model was prepared by injecting an antibody against the Thy-1 cell surface antigen (Thy-1) protein specifically expressed in mesangial cells constituting glomerular cells to induce autoimmunization against Thy-1, leading to cellular death of mesangial cells followed by injury in renal tubules. Generally, the Thy-1 nephritis model is considered to be a renal failure model primarily involving inflammation. AOP-1 gene was injected simultaneously with the Thy-1 antibody and renal function was determined over time on the basis of the blood urea nitrogen. Analysis in comparison with a group untransfected with AOP-1 showed that renal dysfunction was significantly suppressed in the group transfected with AOP-1 gene. Thus, AOP-1 seems to be effective for chronic renal failure.

c. Hepatic Diseases

Hepatic diseases progress to cirrhosis and hepatic failure via viral, alcoholic and drug-induced hepatitis. It can be said that hepatic failure such as cirrhosis is caused by chronic overstress on the liver, which is originally a regenerative organ but fails to regenerate hepatic function. Thus, protection of hepatic cells should be clearly effective for preventing hepatic failure. As shown above, a hepatitis model showed decreased expression of AOP-1, which suggests that administration of AOP-1 may be effective in the same manner as in heart diseases, neurodegenerative diseases and renal diseases.

d. Rheumatism

In rheumatism, synovial cells differentiated into immune cells and proliferated and inflammatory cells in peripheral blood infiltrating into joints induce destruction of cartilage/bone to irreversibly destruct joints. Recently, it has become known that the regeneration of cartilages may be hampered by the apoptosis of chondroblasts under the stress of peroxynitrite (Arthritis & Rheumatism 1999 Vol. 42, No. 7, 1528-1537;J Agric Food Chem. 2001 Vol. 49(8), 3614-21). Analytic results on heart diseases, neurodegenerative disease, renal failure and hepatic failure suggest that the expression of AOP-1 may be decreased under stress threatening the life of cells. Thus, it is anticipated that the expression of AOP-1 may be decreased in chondroblasts and osteoblasts in rheumatic pathologies. Mitochondria are deeply involved in the intracellular cascade of apoptosis. Decreased mitochondrial function may directly trigger apoptosis (General Review: Advanced Medicine, Vol. 54, No. 4, 1999). Our analyses showed that AOP-1 has a protective effect on various cells and tissues. Administration of AOP-1 to chondroblasts and osteoblasts may protect and activate mitochondrial function and suppress the death of chondroblasts and osteoblasts. This makes it possible to maintain the regenerating ability of cartilage/bone.

Consequently, we found novel AOP-1 functions to related cellular protection/activation such as myocardial cellular metabolic activation, protection of myocardial cell function and suppression of myocardial cellular death, neuronal activation and suppression of neuronal death. We also found that administration of AOP-1 is effective for treating diseases associated with decreased expression of AOP-1 gene or AOP-1 such as chronic heart failure, ischemic heart failure, ischemic heart disease, chronic renal failure, neurodegenerative disease and rheumatism, and finally achieved the present invention.

As used herein, "diseases associated with decreased expression of AOP-1 gene or AOP-1" refers to those which contain cells showing decreased expression of AOP-1 gene or AOP-1 in affected tissue (e.g., heart in case of heart failure, neurons in case of brain damage, joints in case of rheumatism). A decrease of AOP-1 is synonymous with decreased intracellular AOP-1 function, so that diseases associated with AOP-1 function decreased by genetic variation can also be included in the scope of the present invention.

The following materials (1) to (4) can be used as active ingredients of prophylactic or therapeutic agents for diseases associated with decreased expression of AOP-1 gene or AOP-1 according to the present invention.

(1) Materials Having the Effect of Enhancing the Expression of AOP-1 Gene

Materials having the effect of enhancing the expression of AOP-1 gene may be any of synthesized or genetically engineered compounds or natural compounds or derivatives thereof, including materials acting on a promoter or enhancer region of AOP-1 gene to enhance the transcription of AOP-1 gene into mRNA or materials having a similar effect via transcriptional factors or the like in cells (e.g. materials binding to a transcriptional factor or a co-activator to promote binding to DNA or another transcriptional factor or co-activator, or materials binding to a transcriptional factor or a co-activator to inhibit binding to DNA or another transcriptional factor or co-activator).

(2) Materials Having the Effect of Enhancing the Production of AOP-1

Materials having the effect of enhancing the production of AOP-1 may be any of synthesized or genetically engineered compounds or natural compounds or derivatives thereof, including a nucleic acid encoding AOP-1 (RNA or DNA; SEQ ID NOS: 1 to 3) or a nucleic acid (RNA or DNA) encoding a polypeptide having an addition, deletion or substitution of one or more amino acids as compared with the amino acid sequence of AOP-1 while retaining the function of AOP-1. A nucleic acid (RNA or DNA) encoding a polypeptide hybridizing to a complementary strand of a nucleic acid encoding AOP-1 (RNA or DNA; SEQ ID NOS: 1 to 3) under stringent conditions while retaining the function of AOP-1 is also included. For example, a nucleic acid hybridizing to it in a solution containing 6×SSC, 0.5% SDS, 10 mM EDTA, 5× Denhardt's solution, 10 mg/ml denatured salmon sperm DNA at 68° C. as described in the literature as standard methods (Molecular Cloning: A Laboratory Manual, Sambrook et al., Cold Spring Harbor Laboratory Press, 1989) is included. Such a nucleic acid preferably has a sequence identity of 90% or more, more preferably 95% or more to a nucleic acid encoding AOP-1 (RNA or DNA; SEQ ID NOS: 1 to 3). Other materials such as modified virus vectors containing these nucleic acids are also suitable. Suitable examples are virus vectors, preferably lentivirus vectors, adeno-associated virus vectors, more preferably adenovirus vectors, or chemically synthesized liposomes, virus envelops or complexes of a virus envelop and a synthetic liposome containing a nucleic acid sequence integrated with AOP-1 gene downstream of a promoter sequence functional in a host cell such as cytomegalovirus promoter (CMV promoter).

Materials binding to AOP-1 mRNA or proteins or nucleic acids inhibiting the degradation of AOP-1 mRNA or materials having the activity of increasing the translation efficiency may also be included similarly to the production of TNF-α own to be regulated by the post-transcriptional stability of mRNA and stabilized by binding of HuR protein.

(3) Materials Having the Effect of Enhancing the Function of AOP-1

AOP-1 scavenges oxidation and peroxynitrite activity by enzymatically reversing redox of active site cysteine residue. Materials having the effect of enhancing the function of AOP-1 may be any of synthesized or genetically engineered compounds or natural compounds or derivatives thereof, including materials binding to this activated cysteine residue to promote redox cycle or materials binding to other than active sites of AOP-1 to promote redox cycle of active sites by allosteric effect. Materials promoting binding of AOP-1 to a target molecule (e.g. receptor) of AOP-1 protein on which AOP-1 protein acts or intracellular signal transduction to enhance the activity of AOP-1 protein are also suitable. For example, thioredoxin protein is known to bind to AOP-1 to increase biochemical antioxidant activity. Materials having efficacy by indirectly enhancing the function of AOP-1 via introduction of proteins enhancing the function of AOP-1 or genes thereof or synthetic induction are also suitable. Materials inhibiting the activity of proteases specifically degrading AOP-1 are also included.

(4) AOP-1 Proteins and Polypeptides Having the Function of AOP-1.

In the present invention, AOP-1 proteins per se or polypeptides having an addition, deletion or substitution of one or more amino acids as compared with the amino acid sequence of AOP-1 while retaining the function of AOP-1 can also be used as active ingredients of prophylactic or therapeutic agents for diseases associated with decreased expression of AOP-1 gene or AOP-1.

(5) Pharmaceutical Preparations

Pharmaceutical preparations containing the materials as described above as active ingredients are prepared using carriers or excipients or other additives used for standard formulation.

Active ingredients of pharmaceutical compositions of the present invention may be free or pharmaceutically acceptable salts thereof. Suitable salts include salts with inorganic acids such as hydrochloric acid, sulfuric acid and phosphoric acid or salts with organic acids such as formic acid, acetic acid, butyric acid, succinic acid and citric acid. Salts with metals such as sodium, potassium, lithium and calcium or salts with organic bases are also suitable.

Preferably, active ingredients are mixed with known pharmacologically acceptable carriers, excipients, diluents or the like and administered in a pharmaceutically conventional manner such as oral administration or parenteral administration including intravenous, intramuscular or subcutaneous administration. Pharmaceutical compositions of the present invention can be prepared by, for example, appropriately mixing an active ingredient with physiologically acceptable carriers, flavoring agents, excipients, stabilizers, diluents, emulsifiers, solubilizing agents, suspending agents, syrups or the like and can be used as tablets, powders, granules, solutions, etc. Tablets can contain additives including, for example, binders such as gelatin and lubricants such as cornstarch, or can be coated with sugar or a gastric or enteric film. Capsules can be prepared by further including liquid carriers in said compositions. Sterile compositions for injection can also be prepared by applying conventional formulations. Aqueous solutions for injection include isotonic solutions containing glucose or the like and can be combined with suitable solubilizers such as polyethylene glycol. They may also contain buffers, stabilizers, preservatives, antioxidants, soothing agents and the like. When active ingredients are susceptible to degradation in the gastrointestinal tract via oral administration, they can be orally administered as formulations less susceptible to degradation in the gastrointestinal tract such as microcapsules enclosing active ingredients in liposomes, for example. They can also be adsorbed via non-gastrointestinal mucosa such as rectal, nasal or sublingual administration. In this case, they can be administered in the form of suppositories, nasal sprays or sublingual tablets.

For use in gene therapy, known vehicles suitable for gene therapy such as virus vectors, preferably lentivirus vectors, adeno-associated virus vectors, more preferably adenovirus vectors, or chemically synthesized liposomes, virus envelops or complexes of a virus envelop and a synthetic liposome can be used in which AOP-1 gene or a nucleic acid for a material enhancing the expression of AOP-1 gene or a material enhancing the production of AOP-1 or a material enhancing the function of AOP-1 has been integrated downstream of a promoter sequence functional in a host cell such as cytomegalovirus promoter (CMV promoter).

When pharmaceutical compositions of the present invention are therapeutically used, therapeutically effective doses are determined for each case depending on the age and the weight of the subject, the severity of the disease and the route of administration and other factors. Typically, the oral dose is about 0.1-1000 mg/adult/day, which may be administered once or divided into several subdoses.

(6) Screening Methods

Materials that can be used as active ingredients of prophylactic or therapeutic agents of the present invention can be screened as follows, for example.

AOP-1 gene or AOP-1 or derivatives thereof used for screening materials enhancing the expression of AOP-1 gene or enhancing the production of AOP-1 may be derived from any sources including mammals such as human (AOP-1 gene: SEQ ID NO: 1, AOP-1: SEQ ID NO: 4), rat (AOP-1 gene: SEQ ID NO: 2, AOP-1: SEQ ID NO: 5) and mouse (AOP-1 gene: SEQ ID NO: 3, AOP-1: SEQ ID NO: 6). Among them, those derived from human are preferably used for studies/developments of prophylactic or therapeutic agents for human. Those derived from animals such as mouse and rat are preferably used for studies/developments using animal models, i.e. non-human transgenic animals having chronic heart failuredue to suppressed or deleted expression of AOP-1 gene. However, those derived from human are desirably used for drug screening using animal models.

Materials enhancing the expression of AOP-1 gene or materials enhancing the production of AOP-1 or materials enhancing the function of AOP-1 are generally screened by methods using a reporter gene. Suitable reporter genes include, for example, chloramphenicol acetyl transferase (CAT), β-galactosidase (β-Gal) and luciferase. Materials enhancing the expression of AOP-1 gene can be screened by, for example, constructing an expression vector having an expression regulatory region (promoter, enhancer or the like region) of AOP-1 gene linked upstream or downstream of the translation region of a reporter gene, transfecting said vector into a suitable culture cell, adding a test material to the culture cell (said material may be any of synthesized or genetically engineered compounds or natural compounds or derivatives thereof) and determining the expression level of the reporter gene or the amount of the reporter protein after a given period. The expression regulatory region of AOP-1 gene (promoter, enhancer and the like region) can be obtained from commercially available genomic libraries by plaque hybridization using a fragment of AOP-1 cDNA as a probe. The amount of the reporter protein can be determined as enzymatic activity or the expression level of the protein using antibodies or the like.

Materials enhancing the production of AOP-1 include DNA containing an AOP-1 sequence or RNA, which can be integrated into a liposome or modified virus vector with similar effects.

Materials enhancing the function of AOP-1 can also be screened by mixing 4 components, i.e. purified AOP-1 or a cell lysate, desirably a mitochondrial fraction and hydrogen peroxide and a reducing agent having a thiol group (e.g. dithiothreitol) and a monitor enzyme having measurable enzymatic activity, and after a given period, determining the activity of the monitor enzyme (Biochemical and Biophysical Research Communications 1994 Vol. 199, No. 1, 199-206; Journal of Biological Chemistry 1996 Vol. 271, No. 26, 15315-15321). Peroxynitrite (obtained by e.g. mixing an acidified nitrite and hydrogen peroxide) is screened by mixing 3 components, i.e. purified AOP-1 or a cell lysate, desirably a mitochondrial fraction and peroxynitrite and a monitor enzyme having measurable enzymatic activity or a substance (e.g. DNA) modified with peroxynitrite, and after a given period, determining the activity of the monitor enzyme or the amount of the substance modified (Nature 2000 Vol. 407, No. 14, 211-215). Thus, materials enhancing the function of AOP-1 can be screened by determining the protective activity of AOP-1 against the deactivation of a monitor enzyme by free radical injury.

(7) Diagnostic Methods, Diagnostic Agents and Diagnostic Kits

AOP-1 gene was shown by us to have an expression level decreased with aggravation of various diseases. The extent of aggravation of chronic heart failure can be known by determining the expression level of AOP-1 gene using a biopsy sample of a patient. For example, the expression level of AOP-1 gene can be determined by isolating total RNA from 100 mg of a biopsy sample of a patient using ISOGEN (Nippon Gene) and treating it with DNase, then synthesizing cDNA, amplifying AOP-1 gene by PCR using suitable primers and determining the strength of the band corresponding to AOP-1 by gel electrophoresis. The expression of AOP-1 gene can also be assayed by any other techniques for assaying RNA or DNA such as the method described in Example 3, Northern hybridization or cDNA array techniques.

As AOP-1 gene was shown by the present invention to be an improving factor of various diseases, it can be readily predicted that individuals having some variation in AOP-1 gene or a regulatory region thereof tend to be susceptible to such disease as chronic heart failure or aggravation in such disease if the function of AOP-1 is lowered or the gene expression level is decreased by the presence of such variation. Thus, risk factors can be diagnosed by testing these variations on the gene. Variations on the gene can be known by isolating DNA from a blood sample of a patient according to standard methods, determining the nucleotide sequence according to the method described in Examples 1-5 and comparing it with the normal sequence. Once the relation between a variation and chronic heart failure has been clarified, the DNA chip or SSCP technique can be applied to detect only such a variation.

Moreover, a biopsy sample of a patient affected with a disease accompanied by chronic heart failure can be used to know the extent of aggravation of chronic heart failure or said disease by determining the AOP-1 level in cardiac myocytes. Suitable assay methods include ELISA or RIA using antibodies against AOP-1, or HPLC or mass spectrometric assays. AOP-1 here may not be in a whole form but may be fragmented so far as it can be assayed.

The present invention also include diagnostic agents or diagnostic kits for chronic heart failure comprising a means for determining the expression level of AOP-1 gene or the production level of AOP-1 using the assay means as described above.

(8) Non-Human Animals and Cells or Tissues Transformed with AOP-1 Gene

Materials of the present invention can be identified by not only the methods as described above in the section (6) Screening methods, but also by using non-human transgenic animals having chronic heart failure or other condition due to suppressed expression of AOP-1. Non-human host animals include small animals such as mouse, rat and rabbit as well as large animals such as dog, pig, sheep and cattle and any other animals expressing the gene and showing the function or physiological action. Gene expression can be suppressed by introducing variation or deletion or the like into a transcriptional regulatory region of AOP-1 or any other means capable of suppressing gene expression. The production of AOP-1 can be suppressed by introducing DNA or RNA complementary to AOP-1 mRNA or a gene encoding the complementary sequence or any other means capable of suppressing the production of AOP-1. Methods for deleting the gene include techniques using embryonic stem cells from knockout mice or any other systems for suppressing the expression of the gene.

The following examples further illustrate the present invention without, however, limiting the invention thereto.

EXAMPLES

Example 1

Search for AOP-1 by Protein Two-Dimensional Electrophoresis of Proteins 1-1. Preparation of Pathologic Model Rats of Chronic Heart Failure and Collection of Left Ventricular Samples A. Dahl Chronic Heart Failure Model Rats Dahl rats are Sprague-Dawley strain rats separated into salt-sensitive rats (Dahl-S) susceptible to hypertension and salt-resistant rats (Dahl-R) resistant to hypertension at the third generation of passage charged with an 8% high salt diet. Kihara et al. of Kyoto University show that Dahl-S rats charged with an 8% high salt diet from 6-weeks of age developed compensatory left ventricular hypertrophy, then left ventricular dilatation accompanied by contraction failure, i.e. uncompensated chronic heart failure, and finally died of pulmonary congestion (Am. J. Physiol., 1994 Vol. 267, H2471-2482). This model can be prepared without any special techniques and can cause chronic heart failure in a short time, and also show clear separation between compensatory hypertrophy stage and uncompensated chronic heart failure stage in each individual, and also show a similar onset process to that of human hypertensive chronic heart failure.

Male Dahl salt-sensitive rats (Dahl-S) (SHIMIZU LABORATORY SUPPLIES) were raised on an 8% high salt diet from 6 weeks of age, and the left ventricle was collected at cardiac hypertrophy stage (11 weeks of age) and chronic heart failure stage (14 weeks of age).

B. Preparation of Abdominal Aortostenotic Rats (Pressure Overload Model: A Pressure Overload-Induced Cardiac Hypertrophy Rat Model or AOB) and Collection of Left Ventricular Samples Sprague-Dawley strain male rats at 9 weeks of age were used for experiments. After the rats were fixed in a prone position and abdominally incised under anesthesia by intraperitoneal administration of sodium pentobarbital (40 mg/kg), the abdominal aorta was exposed and dissected between the right and left renal arteries. A 21 G needle was placed along the aorta and ligated with a silk suture together with the aorta between the right and left renal arteries, and then the needle was pulled out to form aortostenosis. In this model, the systolic blood pressure is raised by such abdominal aortostenosis, thus increasing the afterload of the heart to induce left ventricular hypertrophy. A sham operation group (sham) underwent dissection of the abdominal aorta alone.

The systolic blood pressures at 3 and 17 months after intervention showed higher values than normal, i.e. 232 mmHg and 188 mmHg, respectively, due to arteriostenosis. At month 3, a significant increase in heart weight/body weight ratio was observed and the fractional shortening (FS) indicative of heart function decreased to 26% in rats at month 17 from 52% at month 3. Thus, the left ventricle was collected from both stenotic and sham groups at 3 and 17 months after stenosis formation as samples of compensatory hypertrophy stage and uncompensated chronic heart failure stage, respectively.

C. Preparation of Abdominal Arteriovenous Shunt Rats (Volume Overload Model: A Volume Overload-Induced Cardiac Hypertrophy Rat Model or ACS) and Collection of Left Ventricular Samples Sprague-Dawley strain male rats at 9 weeks of age were used for experiments. After the rats were fixed in a prone position and abdominally incised under anesthesia by intraperitoneal administration of sodium pentobarbital (40 mg/kg), the abdominal aorta and cava were exposed and the bloodstream was stopped by clamping at the aortic bifurcations to the renal artery and the femoral artery. An 18 G needle was inserted into the aorta at the clamped sites to penetrate into the cava, thereby forming an arteriovenous shunt. The needle was pulled out and the wound in the aorta was closed with a surgical adhesive and the clamps were removed. After confirming that arterial blood flows into the vein in the shunt, the abdomen was closed. In this model, the formation of such an abdominal arteriovenous shunt induces an increase in venous pressure, and therefore an increase in cardiac preload to successively impose overload on the right atrium, right ventricle, left atrium and left ventricle, leading to hypertrophy. Moreover, low compliance in the venous system causes blood retention to induce pulmonary congestion. A sham operation group (sham) underwent dissection of the abdominal aorta and cava alone.

Heart function was determined by echocardiography at 3 and 11 months after intervention, and then the animals were dissected to test the heart weight and autopsy findings. Rats at 11 months as compared with 3 months after intervention showed decreased hematocrit levels and pulmonary edema in every case, suggesting advanced volume overload. The right heart system showed an increase in heart weight/body weight ratio or lung weight/body weight ratio, suggesting edema in the region from the right ventricle to the lung. The FS decreased from 57% to 31%. Therefore, the left ventricle was collected from both shunt and sham groups at 3 and 11 months after shunting as samples of compensatory stage and uncompensated chronic heart failure stage, respectively.

D. Preparation of Spontaneously Hypertensive Rats (Pressure Overload Model) and Collection of Left Ventricular Samples SHR rats known as spontaneously hypertensive rats were raised and measured for blood pressure and echocardiogram over time. SHR at 3 months of age showed higher blood pressure and heart weight/body weight ratio than normal and suffered from cardiac hypertrophy due to hypertension. Animals at 19 months of age had appearances such as piloerection and squatting as well as lowered FS from 56% to 32% and lowered systolic blood pressure, and suffered from chronic heart failure. Symptoms such as pleural fluid and edema were also found. The left ventricle was collected by dissection at each stage.

E. Preparation of Model Rats of Heart Failure Following Myocardial Infarction and Collection of Left Ventricular Samples Sprague-Dawley (SD) rats at a body weight of 180 g -200 g were used to ligate the coronary artery. Four weeks after ligation, the heart function was evaluated, and after the heart was isolated, the lung and the heart (right and left ventricles and lung) were weighed. As for the heart function, the end-diastolic pressure and the maximum systolic pressure were determined. In the present model, the vehicle group showed a 3.1-fold increase as compared with the sham group in the end-diastolic pressure, which increases as heart failure becomes worse. The vehicle group showed a 29% decrease as compared with the sham group in the maximum systolic pressure. In the present model, the vehicle group showed a 2.2-fold increase as compared with the sham group in the ratio of the weight of the right ventricle to the body weight, which increases as the heart enlarges. In the present model, the vehicle group showed a 2.3-fold increase as compared with the sham group in the weight of the lung, which increases by congestion as heart function deteriorates. Thus, the present model seems to be a typical heart failure model leading to heart failure via the compensatory stage induced by cardiac hypertrophy following myocardial infarction.

The left ventricular non-infarcted region was collected by dissection.

1-2. Preparation of Protein Samples

To ¼ of the amount of the rat heart was added 1 ml of homogenizing buffer 1 (20 mM Tris HCl, pH 7.4, 1 mM EDTA, 1 mM EGTA, 1 mM PMSF). The tissue was disrupted with a homogenizer and then further sonicated. The supernatant from centrifugation was collected as a soluble protein fraction. The precipitate was washed with the same homogenizing buffer, and then remixed with homogenizing buffer 2 (homogenizing buffer 1+2% triton X100) in the same volume as that of the precipitate and the supernatant after centrifugation was collected as a protein fraction from membrane protein-membrane interaction.

1-3. Protein Assay

A protein assay kit from Pierce based on a simplified BCA was used, in which peptide bonds in proteins chelate divalent copper ions and react with bicinchoninic acid (BCA) to form a purple complex. The bovine serum albumin included in the kit was used as a standard protein.

1-4. Two-Dimensional Electrophoresis

A. One-Dimensional Electrophoresis

Each protein fraction in an amount equivalent to 125-750 μg was suspended in a sample buffer (8 M Urea, 0.5% Triton X-100, 10 mnM DTT, Orange G trace) to swell a dry gel (Immobiline Drystrip from Pharmacia Biotech). Multiphor II from Pharmacia Biotech was used for migration according to the manufacturer's standard protocol. After migration, the gel was stored at −20° C. for a maximum of 1 week and supplied for two-dimensional electrophoresis as needed.

B. Two-dimensional Electrophoresis

The gel was pretreated with an equilibrating buffer (50 mM Tris-HCL, 6 M Urea, 30% glycerol, 1% SDS), and then placed on a polyacrylamide gel. The gel was run using an electrophoresis apparatus from Biorad. Immediately after migration, the protein was immobilized in the gel and simultaneously silver-stained to give a two-dimensional electrophoretogram.

1-5. Comparative Analysis of Protein Expression

The same sample was subjected to at least 2 runs of electrophoresis to pick up proteins showing reproducible expression changes in at least 2 individuals within a group in each model. Among the proteins thus pick up, those showing common changes in many models were taken as chronic heart failure-related proteins. Among them, the protein spots identified as AOP-1 in Example 1-6 below were quantified and shown in the graph of FIG. 1. In FIG. 1, Dahl, AOB, ACS and SHR represent the pathologic model rats of chronic heart failure prepared in 1-1. A to D above.

1-6. Identification of the Protein

A. Recovery of the Protein of Interest from Polyacrylamide Gel

Gel fractions were washed with a suitable buffer to remove SDS. The gel was permeated with trypsin (PROMEGA) so that the protein of interest was digested in the gel and thereby fragmented and eluted from the gel network.

B. Identification of AOP-1 by Mass Spectrometry

The fragments of the protein of interest obtained in A above were analyzed as a mixture using a mass spectrometer from MicroMass (electrospray ionization time-of flight mass spectrometer) to give mass data of the fragments of the protein of interest. Some fragments were further irradiated with helium gas to cleave peptide bonds to give the internal sequence of the protein fragments N'[H(I/L)SVNDL] C' (SEO ID NO: 31 and 32) and mass data (parent ion 1206.6, daughter ions 1069.481, 956.428, 869.418, 770.379, 656.336, 541.324, 428.244). Based on these data, AOP-1 was identified after searches through genetic sequence database available on the Internet (SwissProt Accession No. P20108: SEQ ID NO: 6).

Example 2

Analysis of the Expression of AOP-1 Gene

The left ventricles obtained by the procedure described in Example 1-1, A to D were used as samples.

Total RNA was prepared from each left ventricle using ISOGEN (Nippon Gene) as instructed by the manufacturer and treated with DNase. TaqMan® Reverse Transcription Reagents (PE Applied Biosystems) were used to synthesize cDNA from 1 µg each of the total RNA treated with DNase in 50 µl of the reaction solution. Gene expression was analyzed by a real-time PCR assay system using ABI PRISM 7700 (PE Applied Biosystems). The primers for detecting AOP-1 and the TaqMan® probe were designed on the basis of the nucleotide sequence of mouse AOP-1 cDNA using a primer design software ABI PRISM Primer Express. Forward primer 5'TGCAGTTTCAGTGGATTCCCA3' (SEQ ID NO: 7), reverse primer 5'TTCATGTGGCCCAAACCA3' (SEQ ID NO: 8) TaqMan® probe 5'TCTTGCCTGGATCAACAC-CAAGAAAG3' (SEQ ID NO:9)

Figure 2:
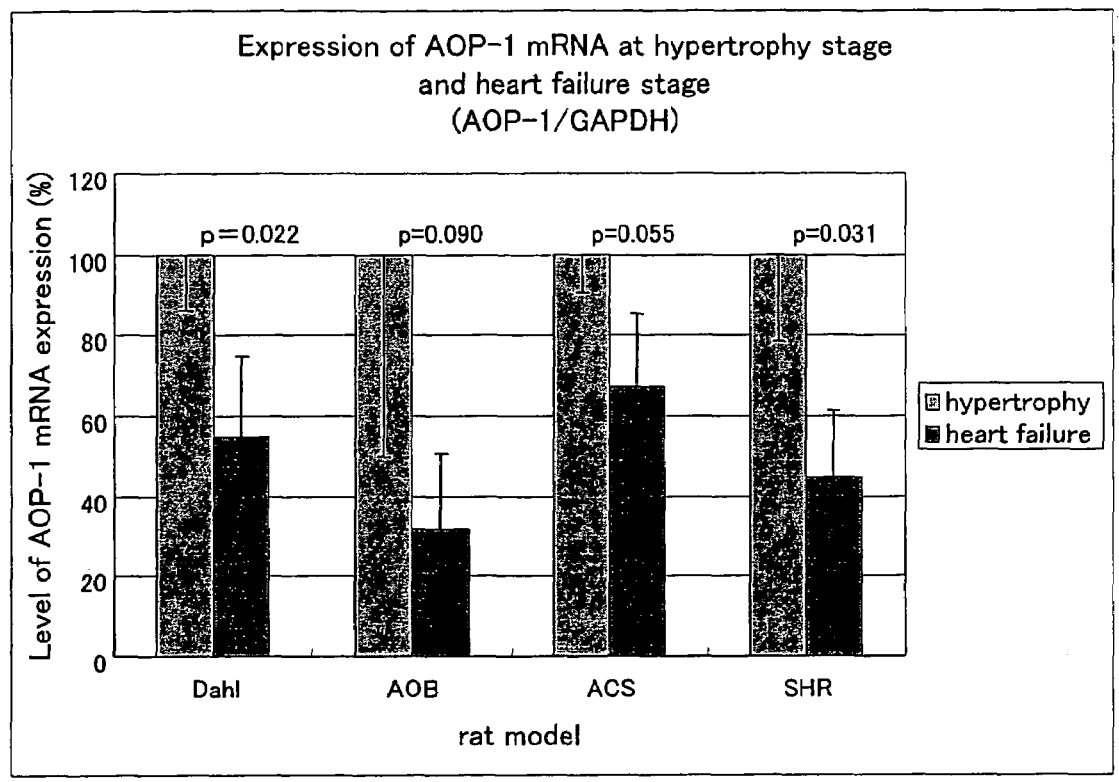
FIG. 2 shows changes in the expression of AOP-1 gene at cardiac hypertrophy stage and heart failure stage in various pathologic model rats of chronic heart failure.

Real-time PCR assay reaction was performed with 1 µl of said cDNA as a template in 40 µl of the reaction solution using TaqMan® Universal PCR Master Mix (PE Applied Biosystems) as instructed by the manufacturer. The expression level of GAPDH was analyzed by the same procedure and used as an internal standard. GAPDH forward primer 5'TGCAC-CACCAACTGCTTAG3' (SEQ ID NO: 24), reverse primer 5'GGATGCAGGGATGATGTTC3' (SEQ ID NO: 25), TaqMan probe 5'CAGAAGACTGTGGATGGCCCCTC3' (SEQ ID NO: 26). GAPDH is one of constitutive proteins and commonly used as an internal standard. The analytic results were shown in FIG. 2. The results showed decreased expression of AOP-1 gene with the progress of the pathology of chronic heart failure in all the models.

Example 3

Analysis of the Expression of TSA (PRx 2), CuZn-SOD, Mn-SOD and Catalase Genes

The left ventricles obtained by the procedure described in Example 1-1, E were used as samples.

Total RNA was prepared from each left ventricle using ISOGEN (Nippon Gene) as instructed by the manufacturer and treated with DNase. TaqMan® Reverse Transcription Reagents (PE Applied Biosystems) were used to synthesize cDNA from 1 µg each of the total RNA treated with DNase in 50 µl of the reaction solution. Gene expression was analyzed by a real-time PCR assay system using ABI PRISM 7700 (PE Applied Biosystems). The primers for detection and the TaqMan® probes were designed on the basis of the nucleotide sequences of rat TSA, CuZn-SOD, Mn-SOD and catalase cDNA using a primer design software ABI PRISM Primer Express. Rat TSA forward primer 5'CCCTCTGCTTGCT-GATGTGACT3' (SEQ ID NO: 10), reverse primer 5'CCTG-TAAGCGATGCCCTCAT3' (SEQ ID NO: 11), TaqMan® probe 5'AGCTTGTCCCAGAATTACGGCGTGTTGAA3' (SEQ ID NO: 12). CuZn-SOD forward primer 5'GCGGAT-GAAGAGAGGCATG3' (SEQ ID NO: 13), reverse primer 5'GCCACACCGTCCTTTCCA3' (SEQ ID NO: 14), TaqMan® probe 5'TGGAGACCTGGGCAATGTGGCTG3' (SEQ ID NO: 15). Catalase forward primer 5'ACGGGTGCT-CAGCCTCC3' (SEQ ID NO: 16), reverse primer 5'AGGCT-TGTGCCCTGCTTC3' (SEQ ID NO: 17), TaqMan® probe 5'CAGCCTGCACTGAGGAGATCCCTCA3' (SEQ ID NO: 18). Mn-SOD forward primer 5'TTACAGATTGCCGCCT-GCTC3' (SEQ ID NO: 21), reverse primer 5'CCAGCAGTG-GAATAAGGCCT3' (SEQ ID NO: 22), TaqMan® probe 5'AATCACGACCCACTGCAAGGAACCA3' (SEQ ID NO: 23).

Figure 3:
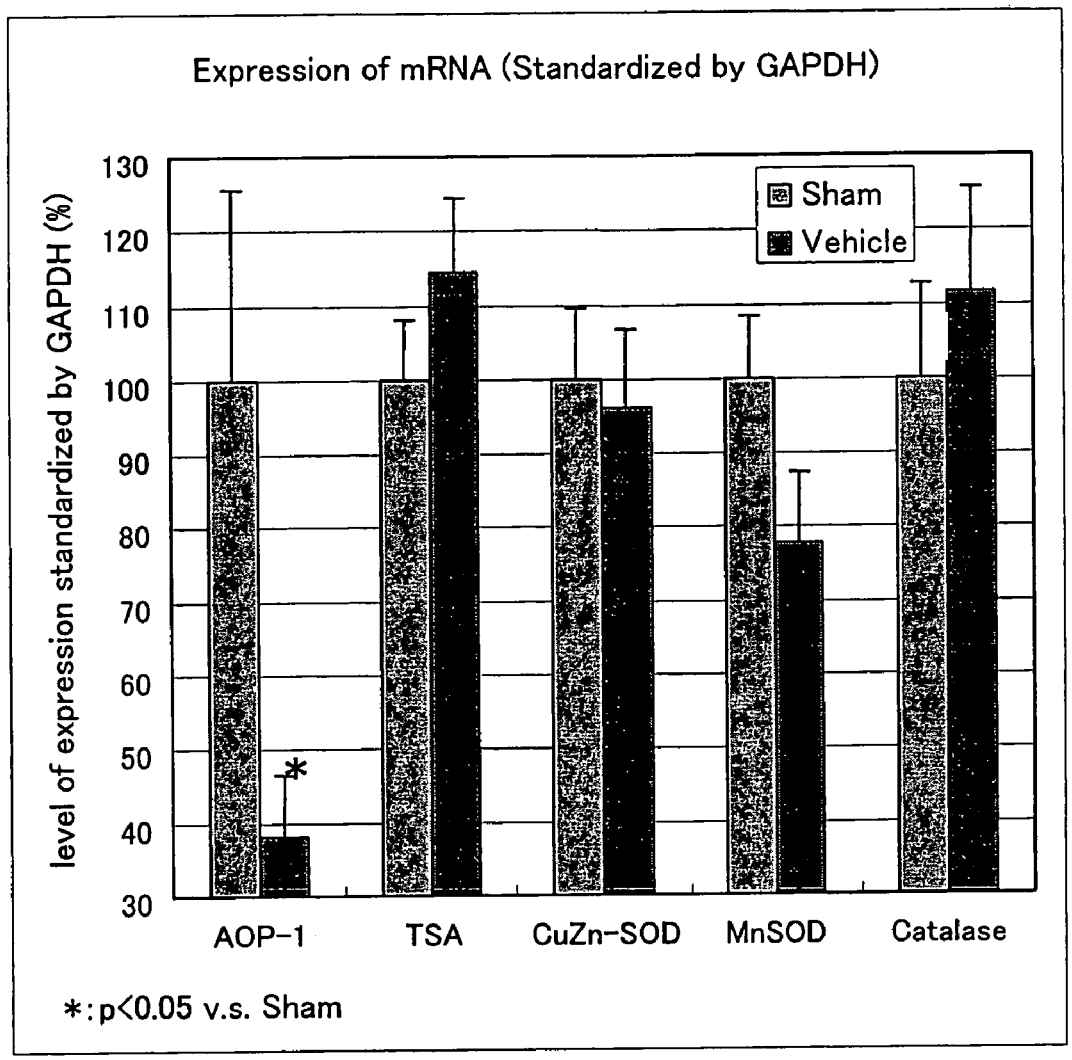
FIG. 3 shows changes in the expression of AOP-1, TSA, CuZn-SOD, Mn-SOD and catalase genes in model rats of chronic heart failure following myocardial infarction.

Real-time PCR assay reaction was performed with 1 µl of said cDNA as a template in 40 µl of the reaction solution using TaqMan® Universal PCR Master Mix (PE Applied Biosystems) as instructed by the manufacturer. The expression level of GAPDH was analyzed by the same procedure and used as an internal standard. The analytic results were shown in FIG. 3. The results showed a significant decrease ($p=0.05$) in the expression of AOP-1 gene in the vehicle group as compared with the sham group but no change in the expression of TSA, CuZn-SOD, Mn-SOD and catalase genes.

Example 4

Cloning of Rat AOP-1 cDNA 4-1. Cloning of a Rat AOP-1 PCR Fragment

PCR was performed using the cDNA prepared in Example 2 as a template together with forward primer 5'AACCGCG-GTCGTGGCTCTTGCGTTCTCT3' (SEQ ID NO: 19) and reverse primer 5'GCGCTAGCTTATTGATGGACCTTCT-CAAAG3' (SEQ ID NO: 20) and the amplification product was TA cloned into a PCR II vector (Invitrogen).

4-2. Sequencing

The nucleotide sequences were determined by analysis on an automatic DNA sequencer model 373A (PE Applied Biosystems) using THERMO Sequenase™ II dye terminator cycle sequencing kit (Amersham Pharmacia). The resulting genetic sequences were compared with GenBank databanks to reveal that one of the clones (pFH1) was a gene identical with rat AOP-1 (GenBank Accession No. AF106944: SEQ ID NO: 2).

Example 5

Construction of a Modified Adenovirus Vector for Expressing AOP-1

5-1. Construction of a Cosmid

The construction of a modified adenovirus vector was performed using an Adenovirus Expression Vector Kit from TAKARA SHUZO. An SacII-NheI fragment containing AOP-1 gene was excised from pFH1 constructed in Example 4, and cloned into pQBI25 (TAKARA SHUZO). Then, the GFP gene was deleted by NheI and BamHI to construct an AOP-1 expression unit having AOP-1 gene downstream of a CMV promoter and a polyA signal from bovine growth hormone downstream thereof. This expression unit was excised with BglII and DraIII and blunt-ended using a DNA Blunting Kit (TAKARA SHUZO) and cloned at the SwaI site of the cosmid pAxcw included in the Adenovirus Expression Vector Kit.

5-2. Preparation and Amplification of a Modified Adenovirus Vector Expressing AOP-1 Using 293 Cells The cosmid described above and the DNA-TPC included in the Adenovirus Expression Vector Kit were co-transfected into 293 cells (Bio Whittaker). In 293 cells, the AOP-1 cosmid and the DNA-TPC are homologously recombined to construct a modified adenovirus vector for expressing AOP-1, which multiplies as a virus through the aid of the E1 protein steadily expressed by 293 cells. Thus prepared modified adenovirus vector expressing AOP-1 lacks the E1 gene so that it can multiply only in cells artificially transformed to constitutively express the E1 gene (e.g. 293 cells).

5-3. Titration of the Modified Adenovirus Vector for Expressing AOP-1

The titration of the modified adenovirus vector for expressing AOP-1 constructed in Example 5-2 was performed according to the protocol as instructed with the Adenovirus Expression Vector Kit.

Example 6

Preparation of Rat Cultured Cardiac Myocytes and Transfection of AOP-1 Gene

Newborn rats at 1-3 days after birth were decapitated under ether anesthesia, and then the heart was removed. The ventricles were isolated and digested with a collagenase (Worthington Biomedical Corporation) to disperse cells. The cells were separated into cardiac myocytes and non-cardiac myocytes by density gradient centrifugation using Percoll (Amersham Pharmacia Biotech). The collected cardiac myocytes were cultured on a D-MEM (low glucose) medium from Nikken Biomedical Laboratory supplemented with fetal bovine serum at a final concentration of 10% (EQUITECH-BIO). The cells were infected with the modified adenovirus vector for expressing AOP-1 prepared in Example 5 at $1.6 \times 10^2$ (M.O.I.) for 1 hour, and then washed twice with the medium. After cultivation for 24 hours, the cells were analyzed in Example 7.

Example 7

Analysis of the Response of Transfected Cells to the Stress of Hypoxic Culture/Reperfusion A modified adenovirus vector for expressing β-galactosidase was prepared in the same manner as described in Example 5 and used for forced expression of β-galactosidase to prepare control cells in the same manner as described in Example 6. These cells were also tested in the following experiment as a control group of forced expression of a protein which does neither harm nor good in a gene transfer system. The cells prepared in Example 6 by forced expression of AOP-1 and the control cells were cultured in a hypoxic culture system for 24 hours, then returned to a normal culture system at an atmospheric oxygen level and 5% carbon dioxide (reperfusion) for 72 hours. A normoxic control group was also prepared by cultivation at a normal oxygen level for 24 hours. The cells cultured under normal oxia, hypoxia and reperfusion after hypoxia were sampled and observed under a microscope. The number of viable cells and the number of autonomously pulsating cells were counted and statistically analyzed. Then, the cell viability and cellular metabolic activity were assayed using MTT reagent (Nacalai Tesque), which is reduced by succinate-tetrazolium reductase systems belonging to the mitochondrial respiratory chain.

Figure 4:
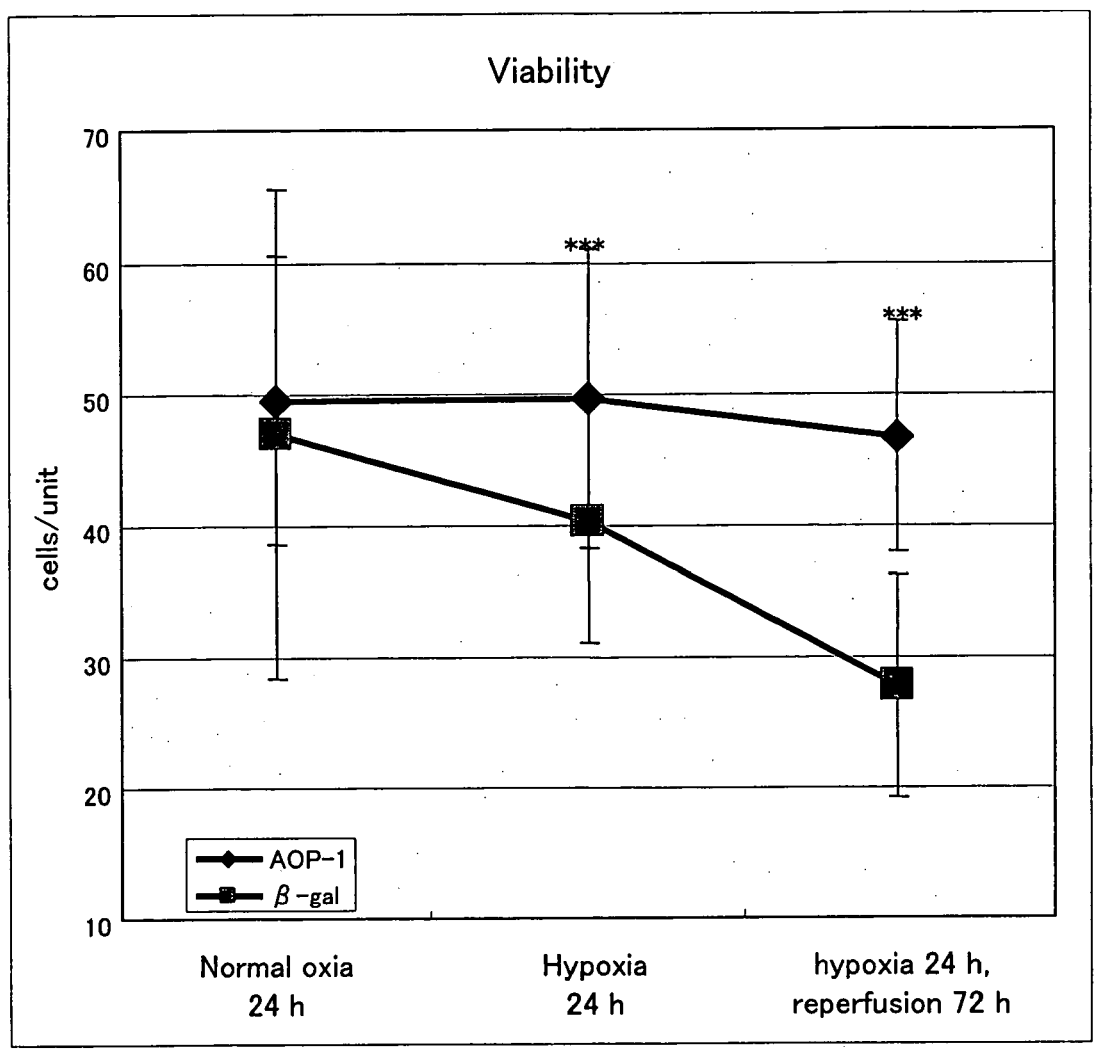
FIG. 4 shows influence of forced expression of AOP-1 gene on cell viability.
Figure 5:
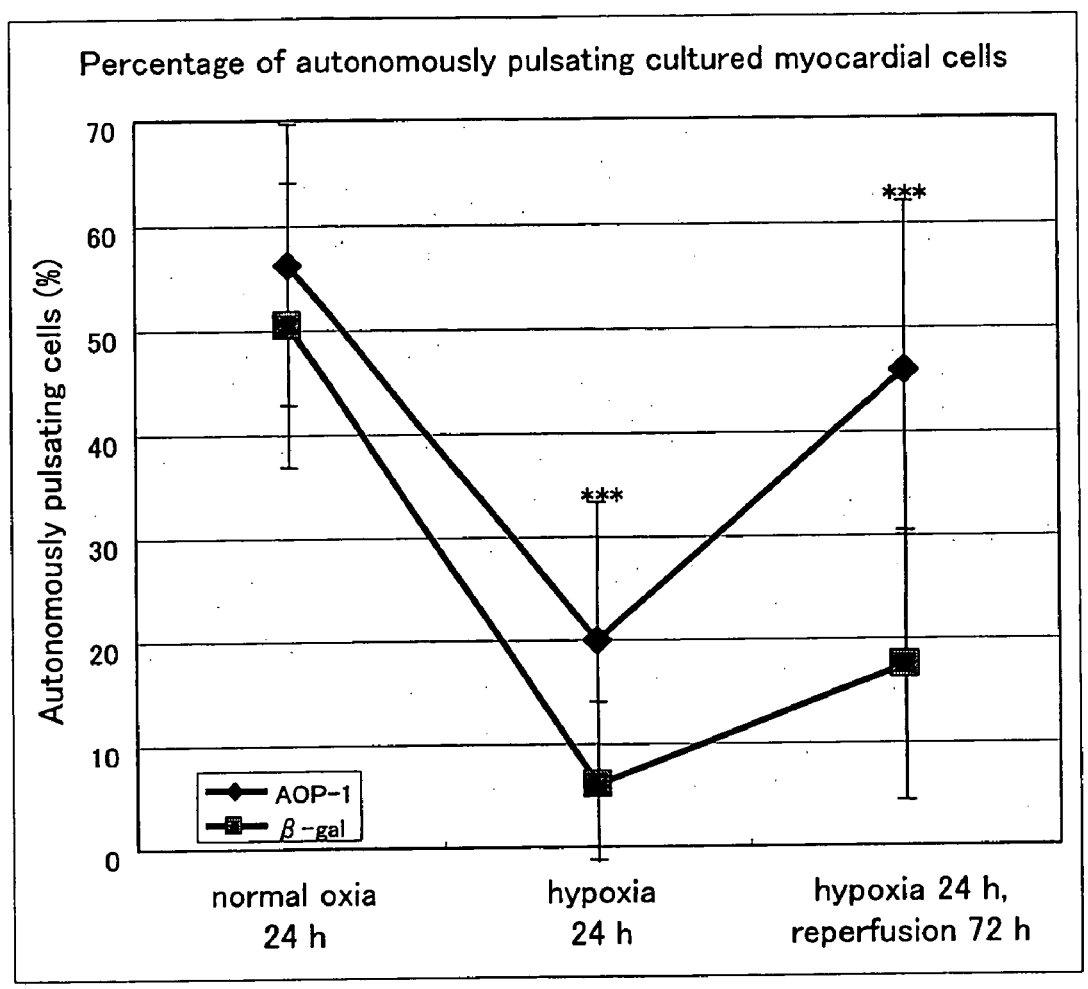
FIG. 5 shows influence of forced expression of AOP-1 gene on the percentage of autonomously pulsating cells.
Figure 6:
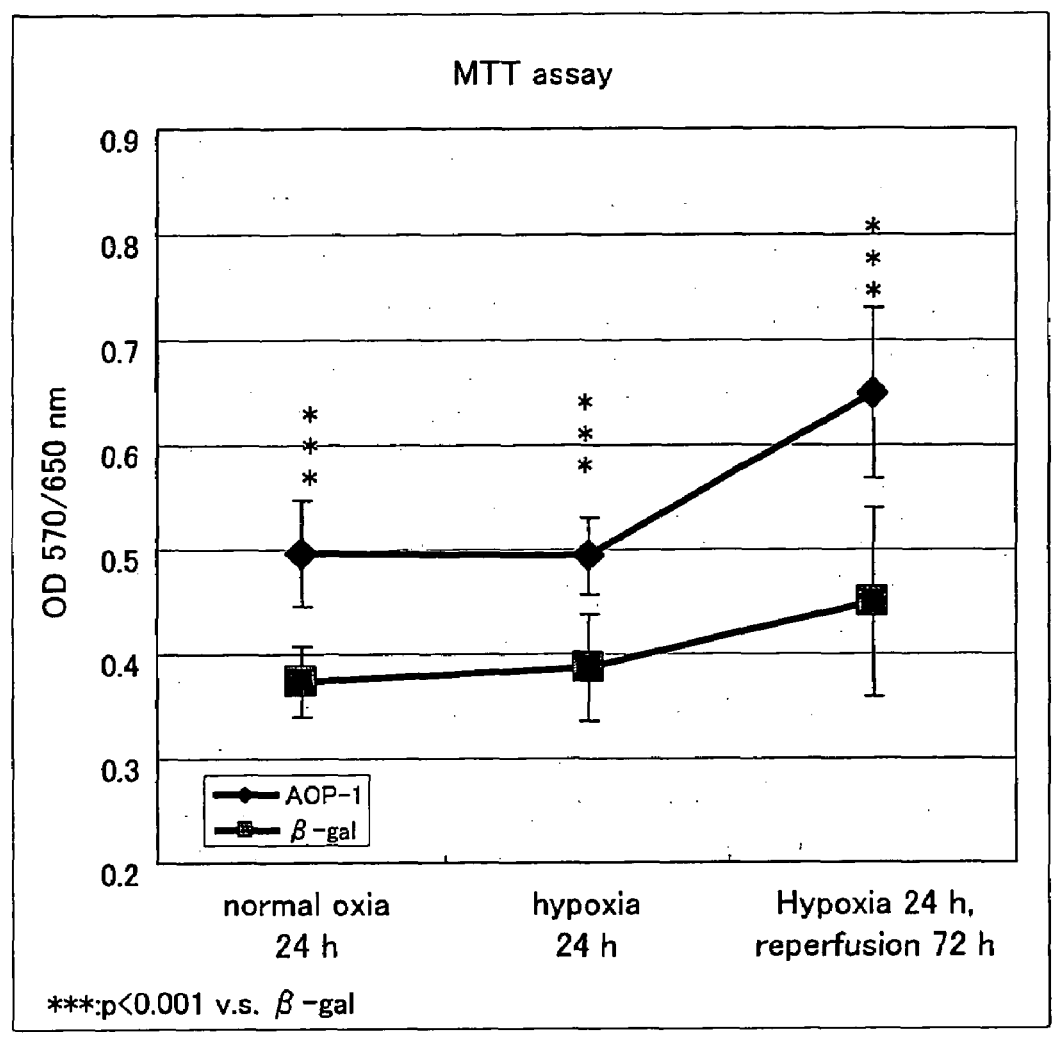
FIG. 6 shows influence of forced expression of AOP-1 gene on MTT reducing activity.

As a result, there was no difference in cell viability between the AOP-1 group and control group cultured under normal oxia, while the AOP-1 group showed a significant increase in cell viability after cultivation under hypoxia for 24 hours and after further cultivation under reperfusion (FIG. 4). The AOP-1 group also showed a significant increase in the percentage of autonomously pulsating cells after cultivation under hypoxia for 24 hours and further cultivation under reperfusion, (FIG. 5). In the MTT assay, the AOP-1 group also showed a significant increase in MTT-reducing activity after cultivation under hypoxia for 24 hours and further cultivation under reperfusion (FIG. 6). Especially, the cellular metabolic function was activated after cultivation under normal oxia, i.e. a non-toxic condition (FIG. 6), suggesting that AOP-1 can improve mitochondrial function.

Generally, it is thought that the aerobic energy production system is replaced by the anaerobic energy production system in hypoxic cells to induce citric acid accumulation or the like, leading to intracellular acidification and intracellular energy depletion. This is because the anaerobic energy production system is more inefficient than the aerobic energy production system. During reperfusion, it is shown that active oxygen species are generated in mitochondria to cause cell injury via oxidation of proteins, DNA, cell membrane phospholipids or the like. The results in the present example demonstrated that AOP-1 eliminates these injuries in cardiac myocytes and has the activity of maintaining normal cellular functions.

As loss of blood flow to cardiac myocytes (ischemia) has been reported to be caused by decreased heart function or cardiac hypertrophy in not only ischemic chronic heart failure (chronic heart failure following myocardial infarction) but also chronic heart failure, a therapeutic drug for chronic heart failure may be provided by supplementing cardiac myocytes in chronic heart failure conditions with the present protein to protect the cardiac myocytes and further maintain the pulsating function.

Example 8

Construction of a Modified Adenovirus Vector for Expressing Antisense AOP-1

AOP-1 gene was excised from the AOP-1 expression unit having AOP-1 gene downstream of a CMV promoter and a polyA signal from bovine growth hormone downstream thereof used in Example 5, and both fragments excised were blunt-ended using a DNA Blunting Kit (TAKARA SHUZO) and ligated again. The direction in which AOP-1 had been cloned was verified by sequencing. This expression unit was excised with BglII and DraIII and blunt-ended using a DNA Blunting Kit (TAKARA SHUZO) and cloned at the SwaI site of the cosmid pAxcw included in the Adenovirus Expression Vector Kit. This was used to prepare a virus vector (adenovirus vector antisense AOP-1 cosmid) in the same manner as described in Example 5.

Example 9

Figure 7:
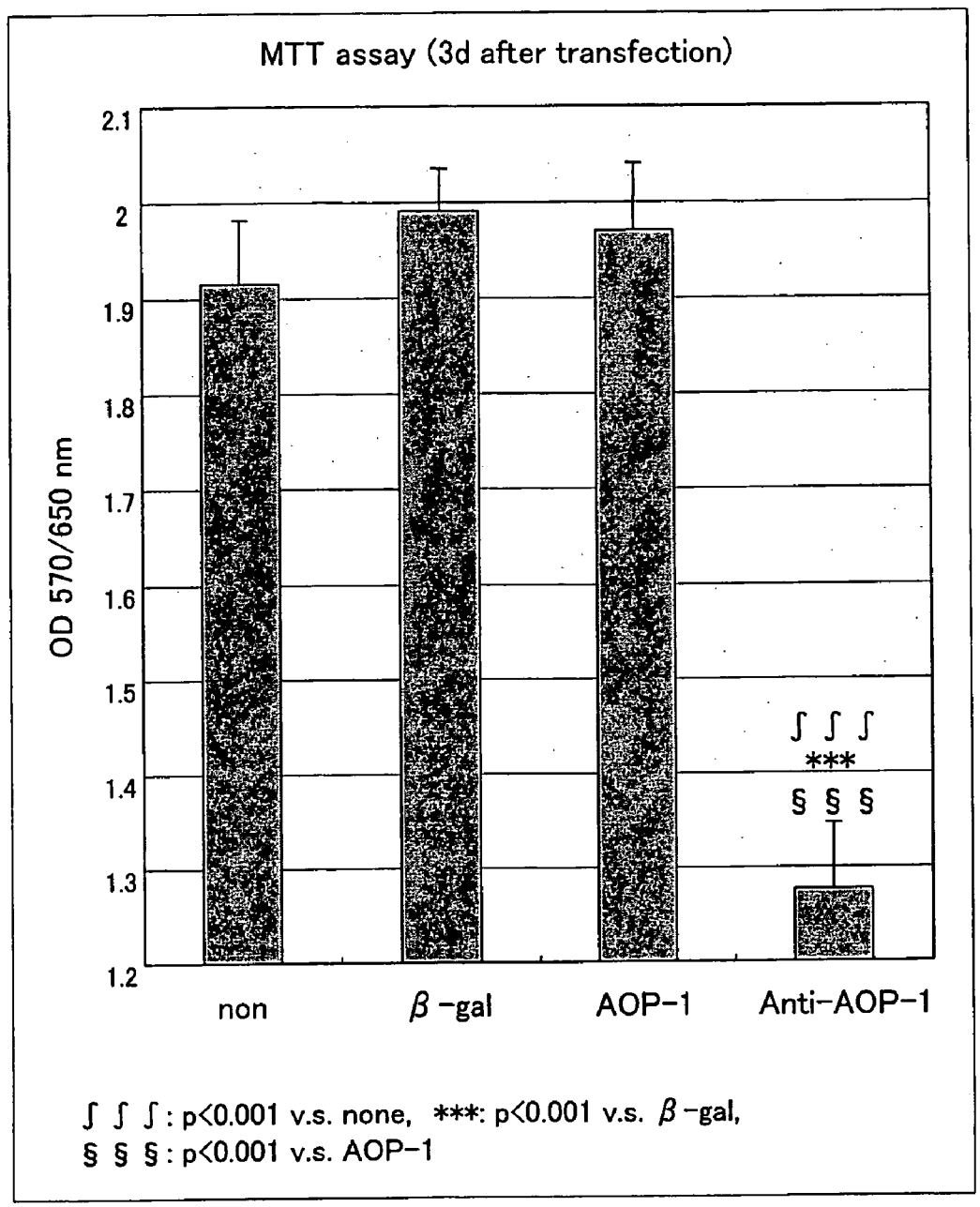
FIG. 7 shows influence of forced expression of antisense AOP-1 gene on cultured cardiac myocytes.

Influence of Forced Expression of Antisense AOP-1 Gene on Cultured Cardiac Myocytes In the same manner as described in Example 6, cells were prepared by forced expression of antisense AOP-1, AOP-1 and β-galactosidase. After the transfected cells were cultured for 72 hours along with untransfected cells, the cell viability and cellular metabolic activity were assayed using MTT reagent (Nacalai Tesque), which is reduced by succinate-tetrazolium reductase systems belonging to the mitochondrial respiratory chain. As a result, the production of reduced MTT reagent was significantly suppressed only in the cell group transfected with antisense AOP-1 (FIG. 7). Microscopic observation showed a significant decrease of the number of viable cells in the antisense AOP-1 group. Thus, the forced expression of antisense AOP-1 was found to adversely affect the viability of cultured cardiac myocytes.

Example 10

Preparation of Other Pathologic Models

A. Preparation of a Nephritis Model

Wistar strain female rats at 8 weeks of age were used. The left kidney was isolated under ether anesthesia. After one hour, nephritis was induced by intravenous administration of 500 μg/rat of anti-Thy-1 monoclonal antibody (1-22-3) (Acta Pathol. Jpn. 36:1191, 1986). The kidney was isolated at various instants (day 1, 4, 7, 14 and 28) after nephritis had been induced.

B. Preparation of a Septic Shock (Infectious Hepatitis) Model

The liver was isolated from three rats weighing 150-300 g at the same weeks of age 2 hours after intraperitoneal administration of 10 mg/kg of lipopolysaccharide.

C. Preparation of a Brain Damage Model

Male Slc Wistar rats (11w) were fixed in a stereotaxic apparatus under Nembutal anesthesia and the skull was exposed and then verified to be horizontal between bregma and lambda and a hole with a diameter of about 0.5 mm was drilled at 4.5 mm posterior and 2.7 mm lateral to bregma. Using a microsyringe, 0.6 μg of ibotenic acid was injected at a depth of 3.0 mm from bregma. After 72 hours, samples for sections were recovered for gene expression analysis. Ibotenic acid is a glutamate analog having specificity to NMDA receptors. Thus, ibotenic acid induces neuronal injury via excessive excitation of NMDA receptors of the two major mechanisms of glutamate injury.

Example 11

Analysis of the Expression of AOP-1 and Other Genes in Other Pathologic Models

Total RNA was prepared from the tissue of each organ obtained in Example 10 above using ISOGEN (Nippon Gene) as instructed by the manufacturer and treated with DNase. TaqMan® Reverse Transcription Reagents (PE Applied Biosystems) were used to synthesize cDNA from 1 μg each of the total RNA treated with DNase in 50 μl of the reaction solution. Gene expression was analyzed by a real-time PCR assay system using ABI PRISM 7700 (PE Applied Biosystems). The primers for detecting AOP-1 and other genes and the TaqMan® probe were designed on the basis of the nucleotide sequence of mouse AOP-1 cDNA using a primer design software ABI PRISM Primer Express. AOP-1 forward primer (SEQ ID NO: 7), reverse primer (SEQ ID NO: 8), TaqMan® probe (SEQ IID NO: 9). TSA forward primer (SEQ ID NO: 10), reverse primer (SEQ ID NO: 11), TaqMan® probe (SEQ ID NO: 12). CuZn-SOD forward primer (SEQ ID NO: 13), reverse primer (SEQ ID NO: 14), TaqMan® probe (SEQ ID NO: 15). Catalase forward primer (SEQ ID NO: 16), reverse primer (SEQ ID NO: 17), TaqMan® probe (SEQ ID NO: 18). Mn-SOD forward primer (SEQ ID NO: 19), reverse primer (SEQ ID NO: 20), TaqMan® probe (SEQ ID NO: 21).

Figure 8A:
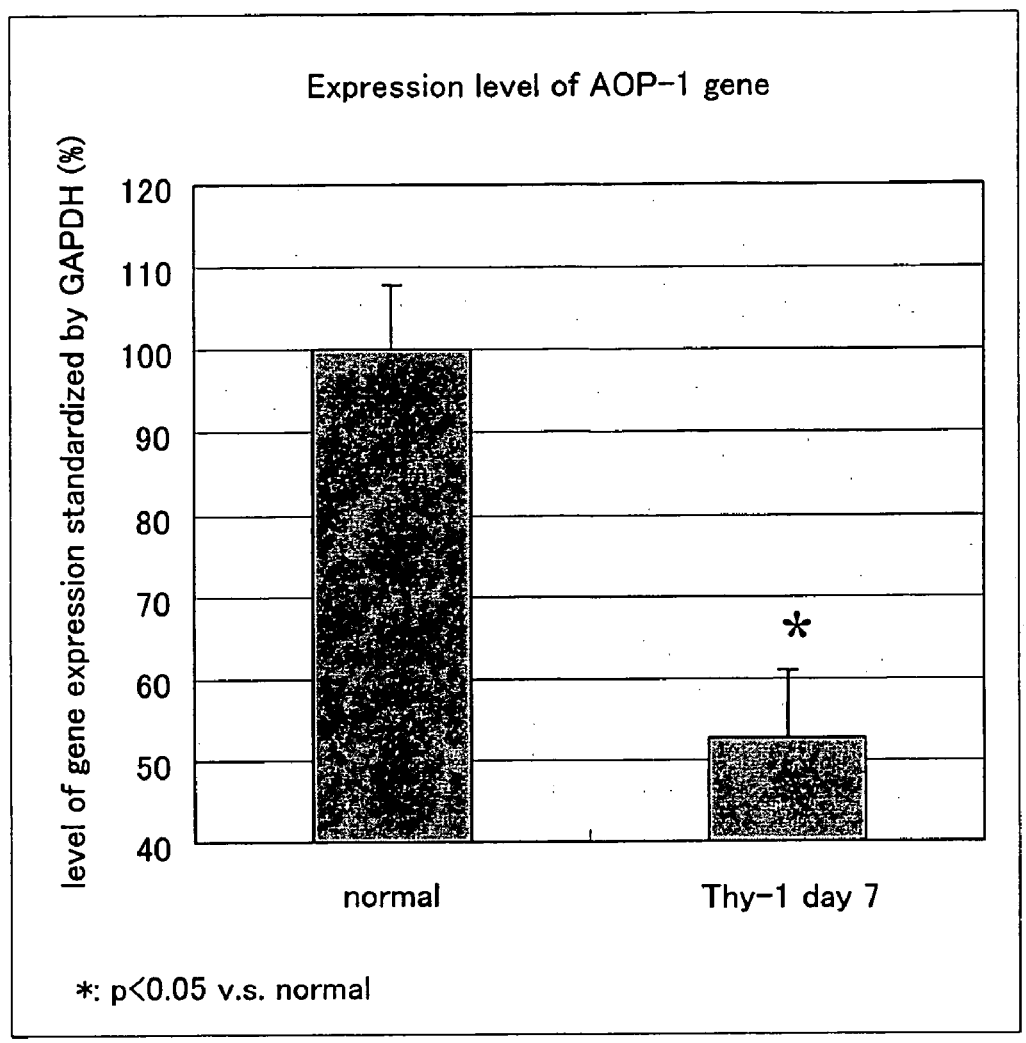
FIG. 8a shows the expression level of AOP-1 gene on day 7 post-inflammation in a nephritis model as compared with a normal control.
Figure 8B:
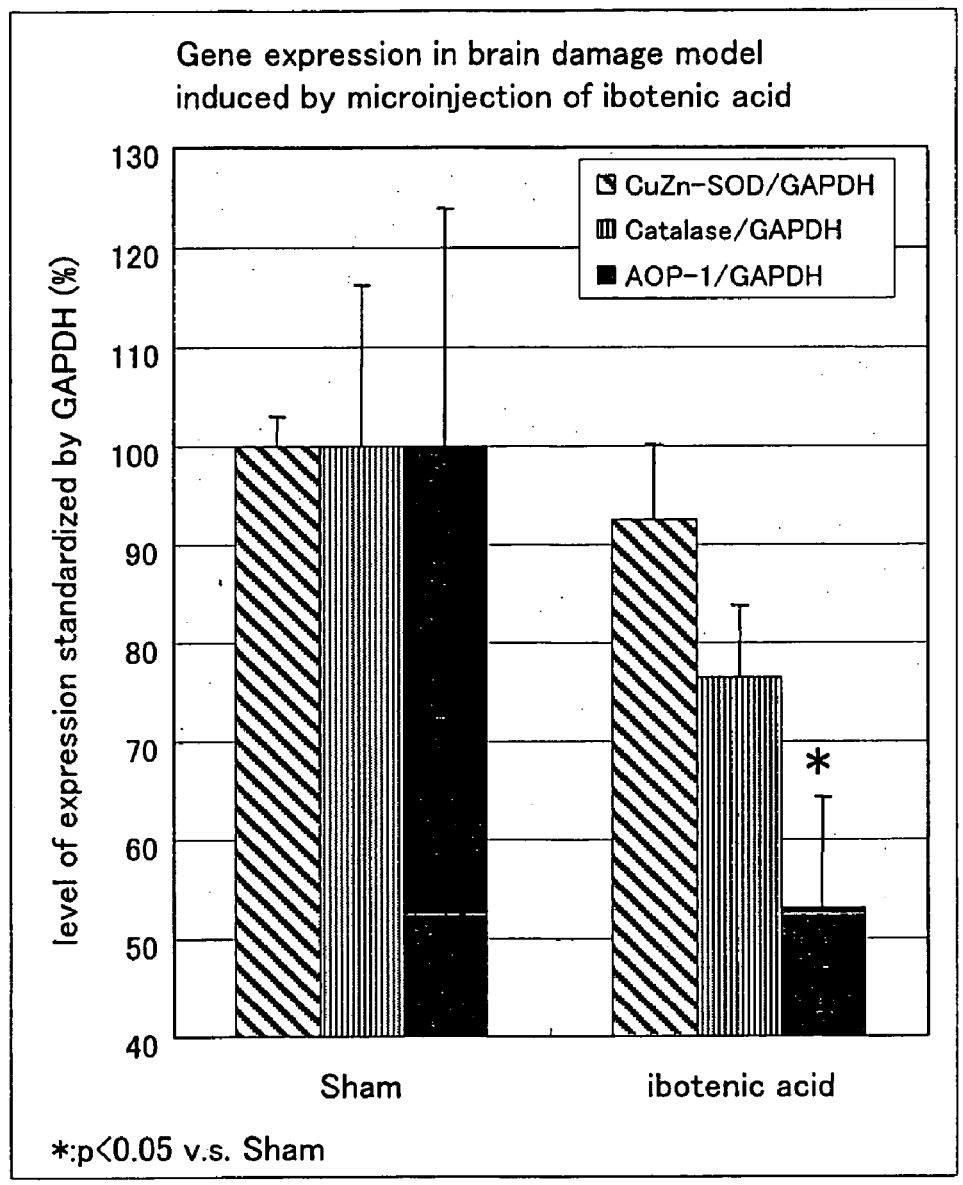
FIG. 8b shows the expression levels of AOP-1, catalase and CuZn-SOD genes in a neurodegenerative disease model induced by microinjection of ibotenic acid as compared with normal controls.
Figure 9:
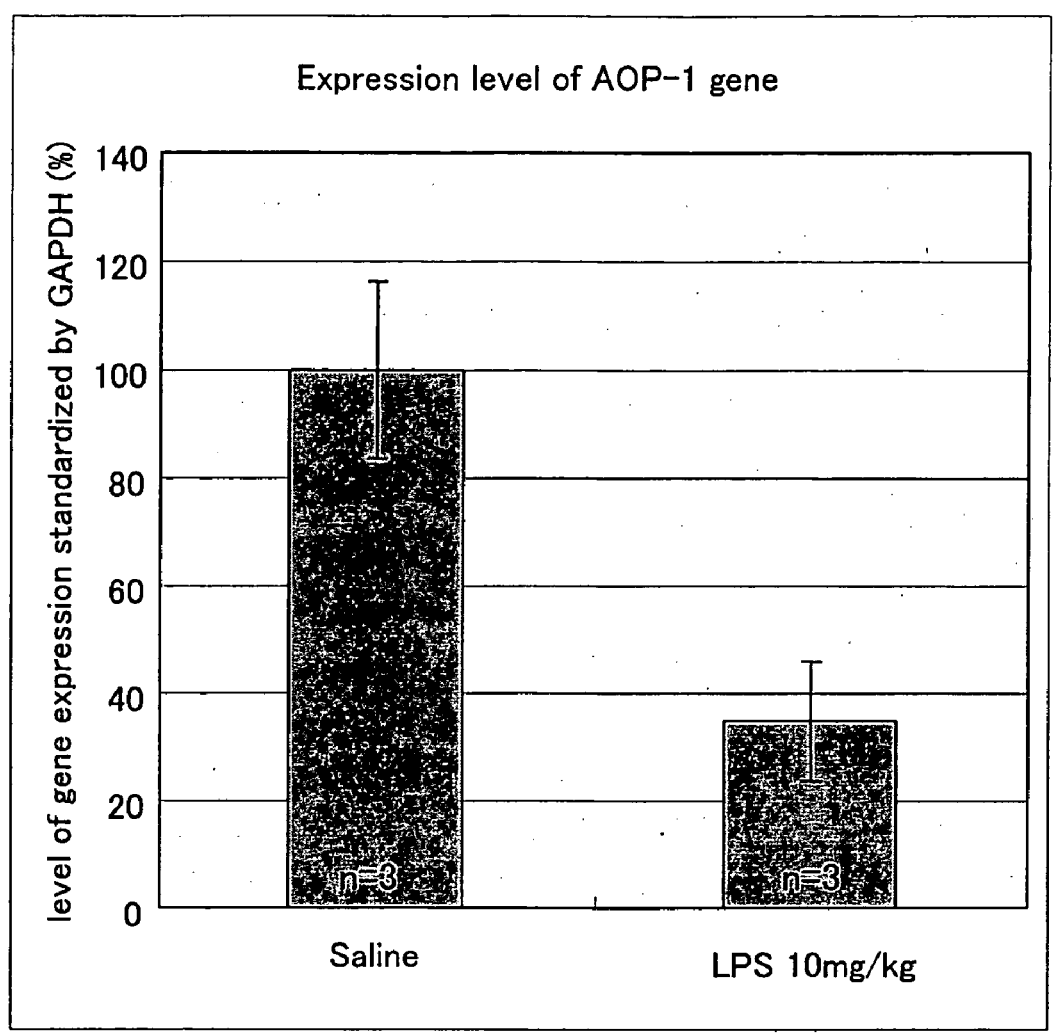
FIG. 9 shows the expression level of AOP-1 gene in an infectious hepatitis model as compared with a normal control.

Real-time PCR assay reaction was performed with 1 μl of said cDNA as a template in 40 μl of the reaction solution using TaqMan® Universal PCR Master Mix (PE Applied Biosystems) as instructed by the manufacturer. The expression level of GAPDH was analyzed by the same procedure and used as an internal standard. The analytic results were shown in FIG. 8*a* (nephritis model), FIG. 8*b* (brain damage model) and FIG. 9 (infectious hepatitis model). The results showed decreased expression of AOP-1 gene with the progress of the pathology in the affected organ of each pathologic model.

Example 12

Preparation of Cultured Fetal Rat Neurons

Wistar strain rats on gestation days 18-20 were anesthetized with ether and then abdominally incised. The embryo was removed from the uterus and the brain was isolated from the embryo and stored in ice-cooled HBSS (Hanks for tissue culture "Nissu" (2) (Nissui Pharmaceutical) 9.8 g/l, NaHCO$_3$ 0.35 g/l; filter sterilized). Immediately, the cerebrum was separated under a stereomicroscope and cells were dispersed with a proteolytic enzyme papain (Worthington). Neurons were collected and cultured on a D-MEM (high-glucose) medium from Nikken Biomedical Laboratory supplemented with horse serum at a final concentration of 10%. On day 4 after cultivation started, the serum-containing medium was added and the cells were cultured for further 3 days. After cultivation for a total of 7 days, the AOP-1 or β-galactosidase adenovirus vector was transfected. Cultivation was continued for 48 hours after transfection to induce stimulations such as glutamate injury or serum deprivation.

Example 13

Figure 10:
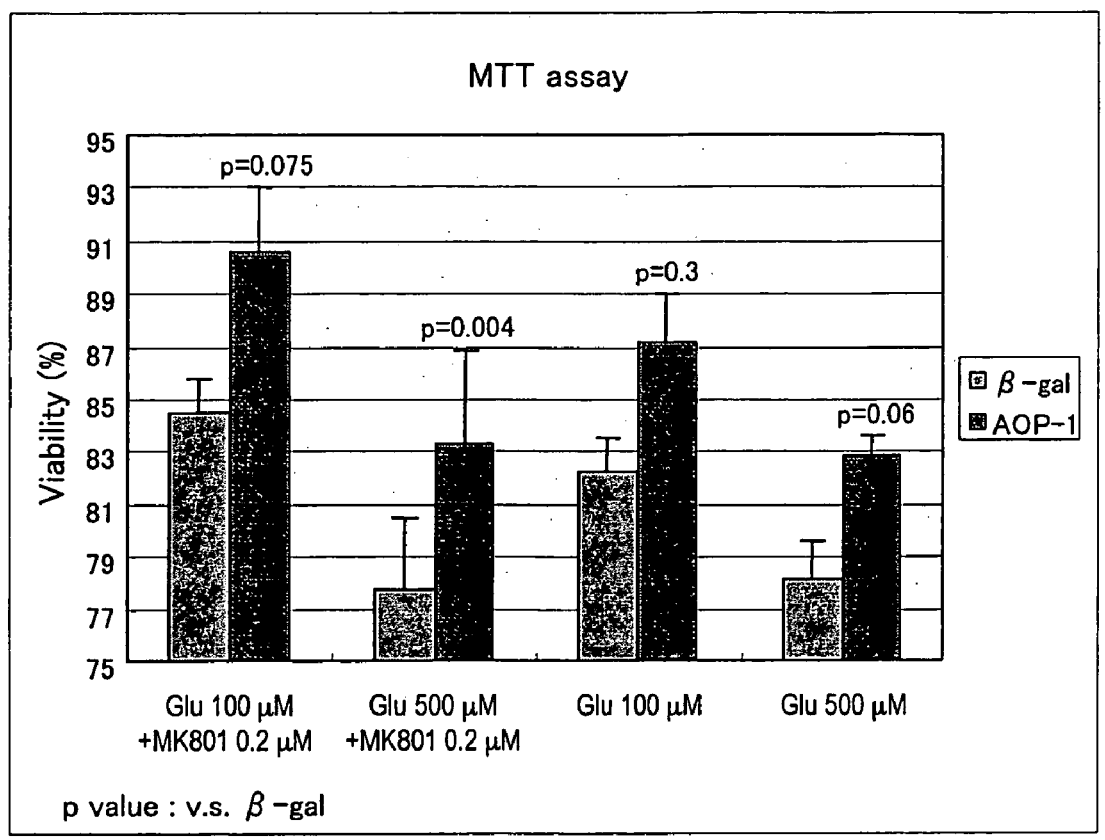
FIG. 10 shows the protective effect of forced expression of AOP-1 gene on glutamate injury in cultured neurons.

Detection of the Protective Effect of AOP-1 against Glutamate Injury in Cultured Neurons The cultured neurons prepared in Example 12 were transfected with AOP-1 gene in the same manner as in Example 6. A control group of forced expression of β-galactosidase was used as a in the following experiment in the same manner as in Example 7. The cultures were incubated with glutamate at final concentrations of 0, 100 and 500 μM for 48 hours and then tested by the MTT assay. The ratio of the MTT value of the glutamate injury group to that of the non-glutamate group in each transfected group was shown as neuroprotection rate in a graph (FIG. 10). In FIG. 10, MK-801 means (+)-dibenzocycloheptenеimine, which is an NMDA receptor antagonist shown to protect cultured neurons against glutamate injury (EurJ Pharmacol 1993 Vol. 248(4) 303-312). As shown in the figure, the AOP-1 transfected group showed a tendency to protect cultured neurons in the non MK-801 group as compared with the group transfected with β-galactosidase. Moreover, it showed a significant protective effect for cultured neurons in the MK-801 group as compared with the group transfected with β-galactosidase, indicating that AOP-1 has an additive effect on the protective effect of MK-801. Two types of glutamate injury have been found in neurons, i.e. calcium overload mediated by the NMDA receptors described above and intracellular cystine depletion mediated by the activation of cystine/glutamate antiporter (Neuroscience 1992 Vol. 48(4) 906-914). These results suggest that AOP-1 has a protective effect against both types of injury at the same time.

Example 14

Figure 11:
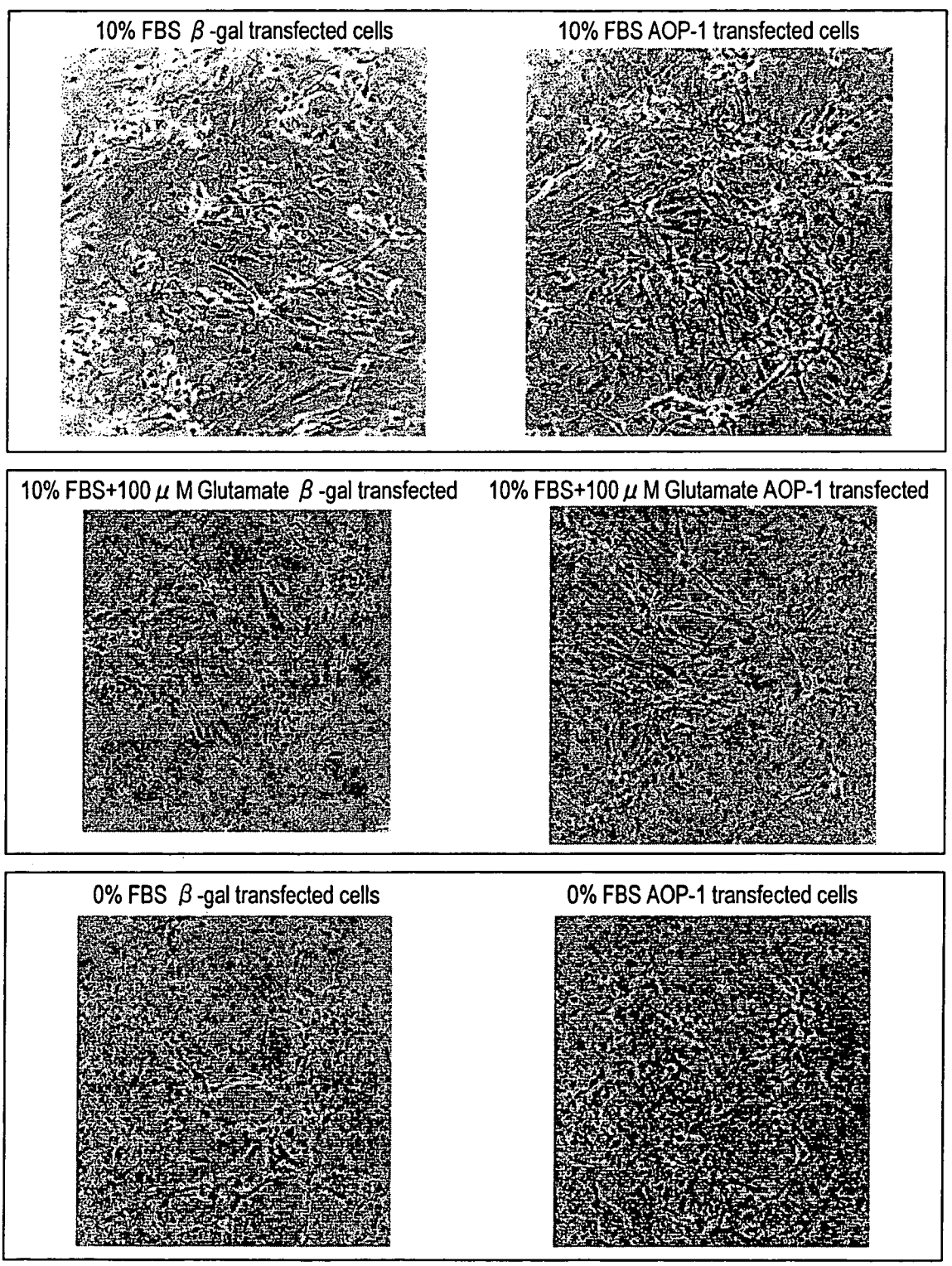
FIG. 11 shows the neurite outgrowth promoting/protecting effect of forced expression of AOP-1 gene on cultured neurons.

Detection of the Neurite Outgrowth Promoting Effect of AOP-1 on Cultured Neurons Cells with no glutamate added (10% FBS group), glutamate added (10% FBS group+100 μM glutamate group) and serum deprived (0% FBS group) in Example 12 were photographed (FIG. 11).

The AOP-1 group consistently showed neurite outgrowth promoting and protecting effects in the presence of various stimulations.

Example 15

Comparison of the Protective Effects of AOP-1, TSA and CuZn-SOD on Cultured Cardiac Myocytes The rat TSA was obtained and sequenced by the procedure described in Example 4 (SEQ ID NO: 27). SEQ ID NO: 28 represents the protein sequence translated from SEQ ID NO: 27. CuZn-SOD represents a plasmid (pYSO200) containing human CuZn-SOD gene (SEQ ID NO: 29) described in the literature (FEBS letter 1990 Vol. 20:269(1) 89-92) as obtained from the author. SEQ ID NO: 30 represents the protein sequence translated from SEQ ID NO: 29. The procedure described in Example 5 was applied to each gene to prepare a modified adenovirus vector for expressing TSA and a modified adenovirus vector for expressing CuZn-SOD. Cultured cardiac myocytes were prepared by the procedure described in Example 6 and transfected also by the procedure described in Example 6. Resistance to stress was analyzed as follows.

1) Cell Viability under Hypoxia

Figure 12A:
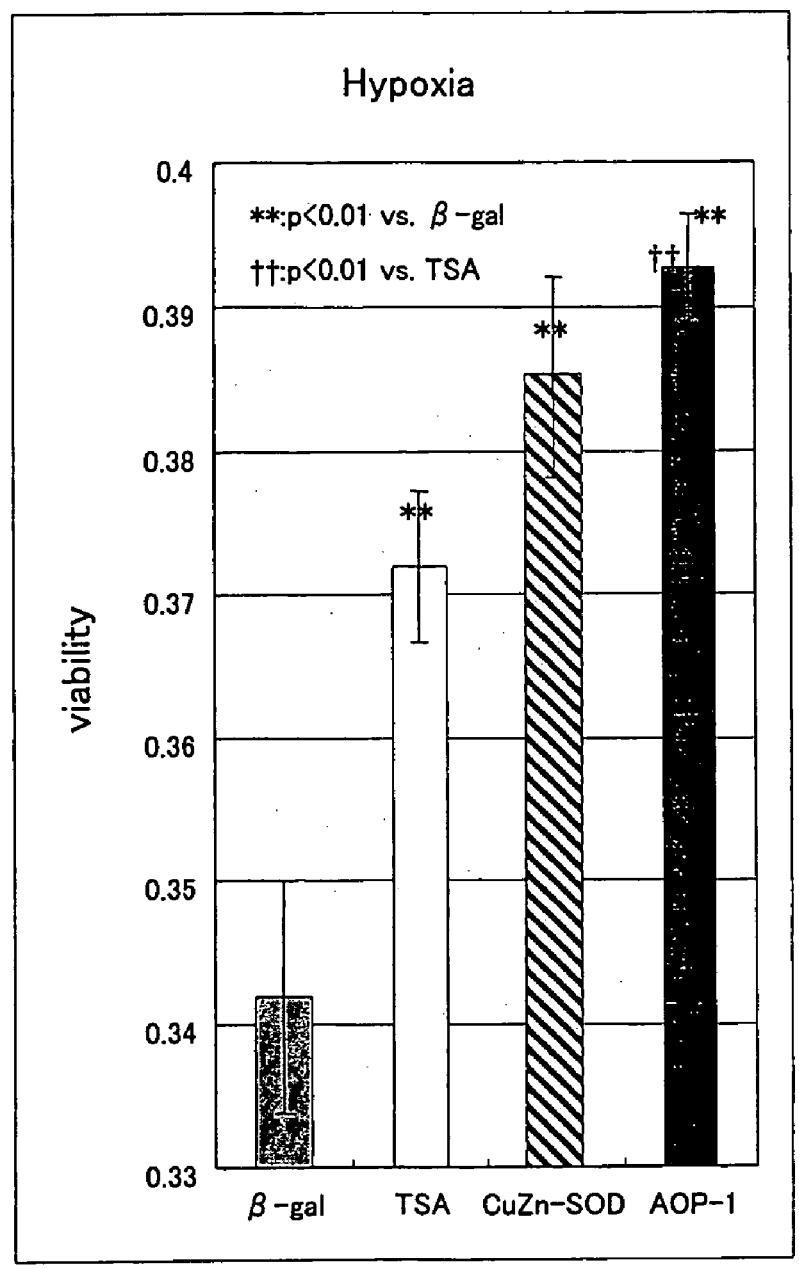
FIG. 12a shows the viabilities of cells transfected with AOP-1, TSA and CuZn-SOD under hypoxia.

Cells cultured for 24 hours post-transfection were exposed to hypoxia and further cultured for 24 hours. The cell viability was determined by the MTT assay described in Example 7. Cells transfected with AOP-1, TSA and CuZn-SOD genes showed a significantly increased viability (p<0.01) as compared with control (cells transfected with β-galactosidase). Cells transfected with AOP-1 gene showed a significantly increased viability as compared with cells transfected with TSA and further showed a tendency to increase viability as compared with cells transfected with CuZn-SOD (FIG. 12a).

2) Cell Viability under Hydrogen Peroxide

Figure 12B:
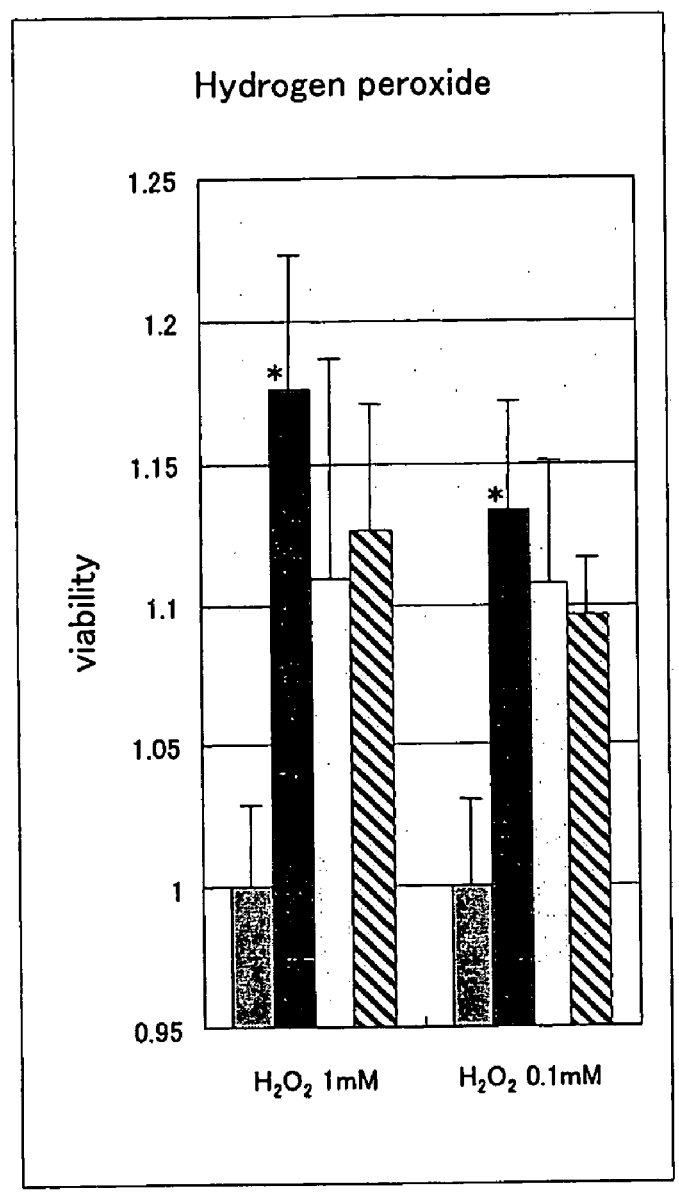
FIG. 12b shows the viabilities of cells transfected with AOP-1, TSA and CuZn-SOD under exposure to hydrogen peroxide.

Cells cultured for 24 hours post-transfection were exposed to 0.1 and 1 mM hydrogen peroxide and further cultured for 24 hours. The cell viability was determined by the MTT assay described in Example 7. Cells transfected with AOP-1 gene showed a significantly increased cell viability as compared with control (P<0.05). However, the groups transfected with TSA and CuZn-SOD showed a tendency to improve cell viability but not statistically significant (p<0.05) (FIG. 12b).

3) Cell Viability under High-Glucose Culture Condition

Cells cultured for 24 hours post-transfection were exposed to 30 mM glucose (about 6-fold excess of normal level) and further cultured for 24 hours. The cell viability was determined by the MTT assay described in Example 7. Cells transfected with AOP-1 gene showed a significantly increased cell viability as compared with control (P<0.05). However, the group transfected with CuZn-SOD showed a tendency to improve cell viability but not statistically significant.

Figure 12C:
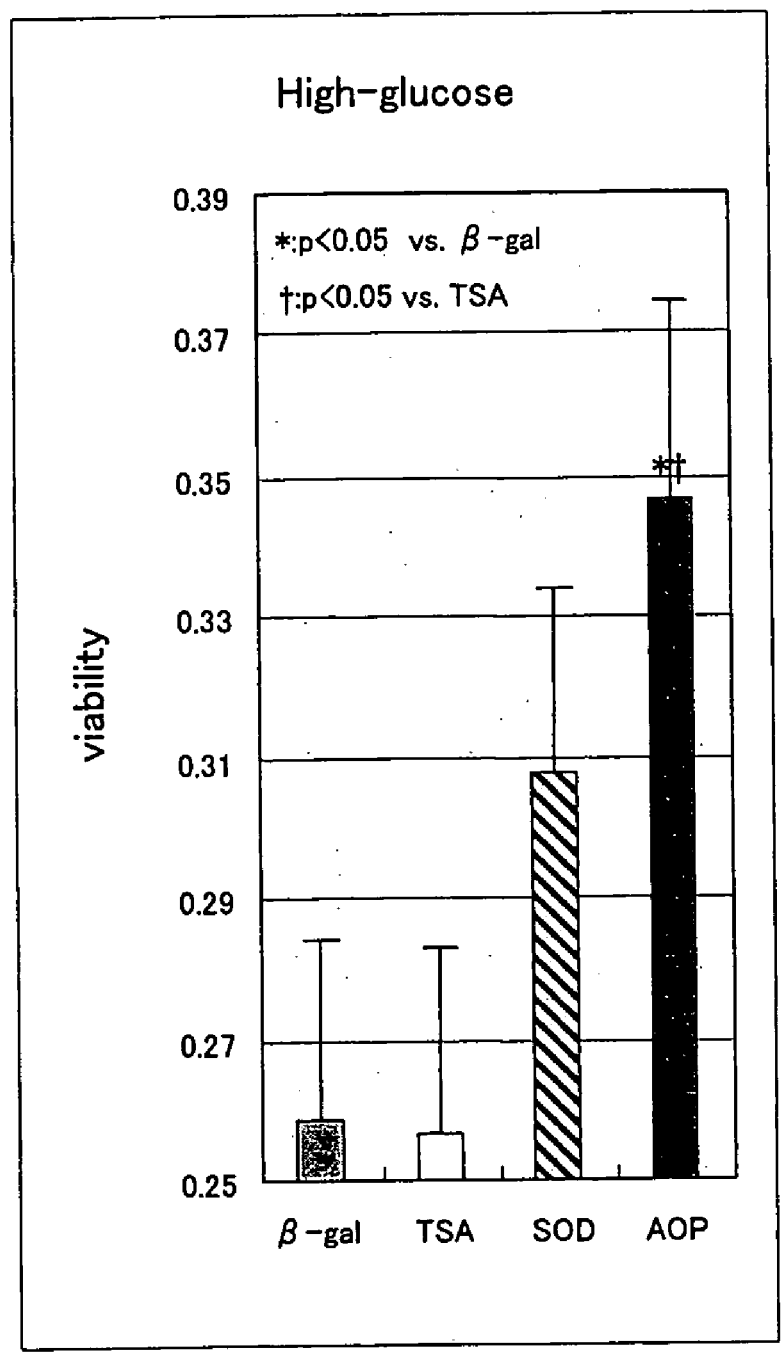
FIG. 12c shows the viabilities of cells transfected with AOP-1, TSA and CuZn-SOD under high-glucose condition.

Cells transfected with TSA gene showed no difference from control in viability (FIG. 12c). Cultivation on high glucose media is thought to closely mimic the hyperglycemic condition in diabetes, suggesting that AOP-1 may also be effective for complications associated therewith.

Example 16

Protective Effect of AOP-1 on the Heart

The rat heart was infected with the modified adenovirus vector for expressing AOP-1. In parallel, a sham group was prepared by infection with a diluent (saline) alone. The infection protocol was as described in the literature (Circulation 2001 Vol. 104 1424-1429). The animals were raised for 4-5 days post-infection, and then subjected to ischemic reperfusion experiments by the Langendorff's method. Under anesthesia with pentobarbital-Na (50 mg/kg, i.p.), heparin (500 U/kg) was administered via the tail vein. After the chest was open, the heart and lung were removed and a canula was inserted into the aorta, which was then perfused by the Langendorff's method (perfusion at a constant pressure of 70 mmHg). A latex balloon connected to a piezotransducer was inserted from the auricle of left atrium into the left ventricle to measure the left ventricular pressure. Water was charged into the balloon until the left ventricular end-diastolic pressure reached about 5 mmHg. The perfusion solution used was a modified Krebs-Henseleit bicarbonate buffer (in mM: NaCl 118, KCl 4.7, $CaCl_2$ 1.25, $MgSO_4$ 1.2, $KH_2PO_4$ 1.2, $NaHCO_3$ 25.0, glucose 11.0). The right atrium was paced with a pacemaker at about 280 bpm to keep the heart rate constant.

The perfusion solution was stopped for 35 minutes to induce ischemia and then perfusion was resumed to form ischemic reperfusion injury. The left ventricular pressure was measured before ischemia and 30 minutes after reperfusion to determine the heart function recovery factor. The time from the start of ischemia to ischemic rigidity was also determined. Ischemic rigidity is shown to highly correlate to ATP depletion in cardiac myocytes (J Mol Cell Cardiol 1996, Vol. 28, 1045-1057). Necrotic myocardial cell levels were also compared by measuring lactate dehydrogenase (LDH) activity released into the heart perfusate (1-30 minutes post-reperfusion).

Figure 13A:
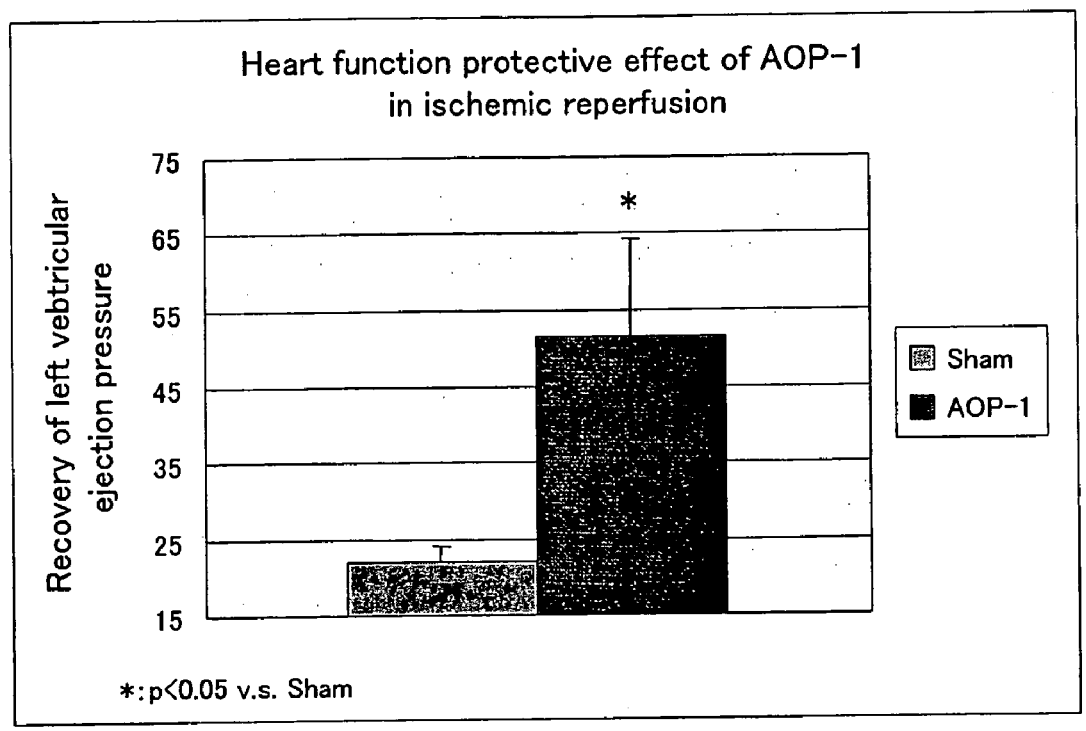
FIG. 13a shows the heart function protective effect of AOP-1 in ischemic reperfusion.
Figure 13B:
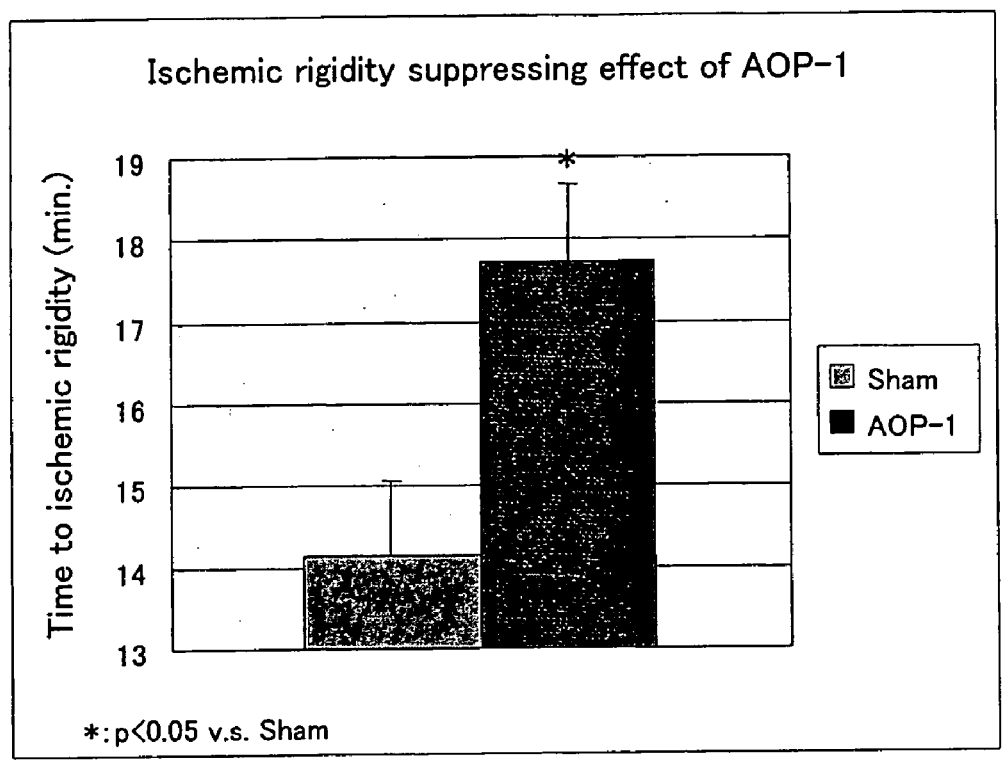
FIG. 13b shows the ischemic rigidity suppressing effect of AOP-1 in ischemic reperfusion.
Figure 13C:
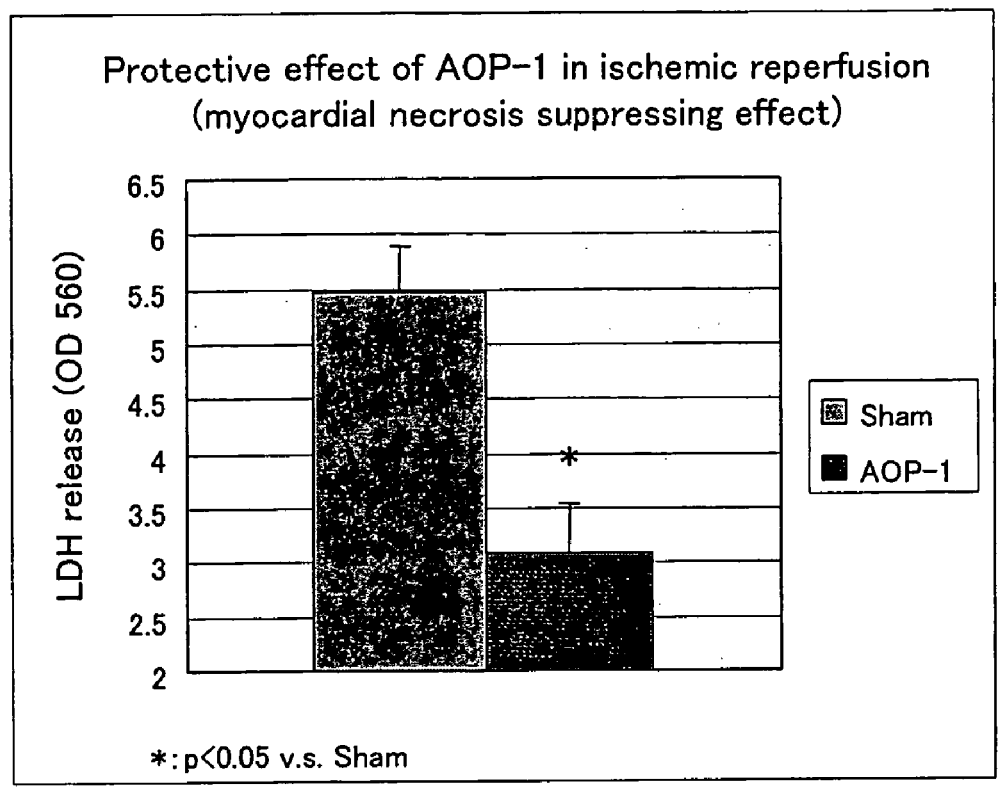
FIG. 13c shows myocardial necrosis suppressing effect of AOP-1 in ischemic reperfusion.

The heart subjected to forced expression of AOP-1 showed significantly better function recovery during reperfusion as compared with the heart of the sham group subjected to simple transfection (FIG. 13a). The time from ischemia to ischemic rigidity was significantly extended in the heart subjected to forced expression of AOP-1 as compared with the control group (sham group) (FIG. 13b). This shows that AOP-1 suppressed ATP decrease in cardiac myocytes during ischemia. After ischemic reperfusion, the LDH activity released into the heart perfusate was measured to show that LDH release was significantly suppressed in the AOP-1 group as compared with the control group (FIG. 13c). LDH release is a common marker protein correlated to cell injury/necrosis (Am J Physiol 2001, Vol. 280, H 2313-2320). Thus, AOP-1 seems to have suppressed cell necrosis during reperfusion. This result showed that AOP-1 protects against both ischemic injury and reperfusion injury not only in cultured cells but also in vivo via novel mitochondrial activation in addition to antioxidation.

Example 17

Protective Effect of AOP-1 on the Brain

Figure 14A:
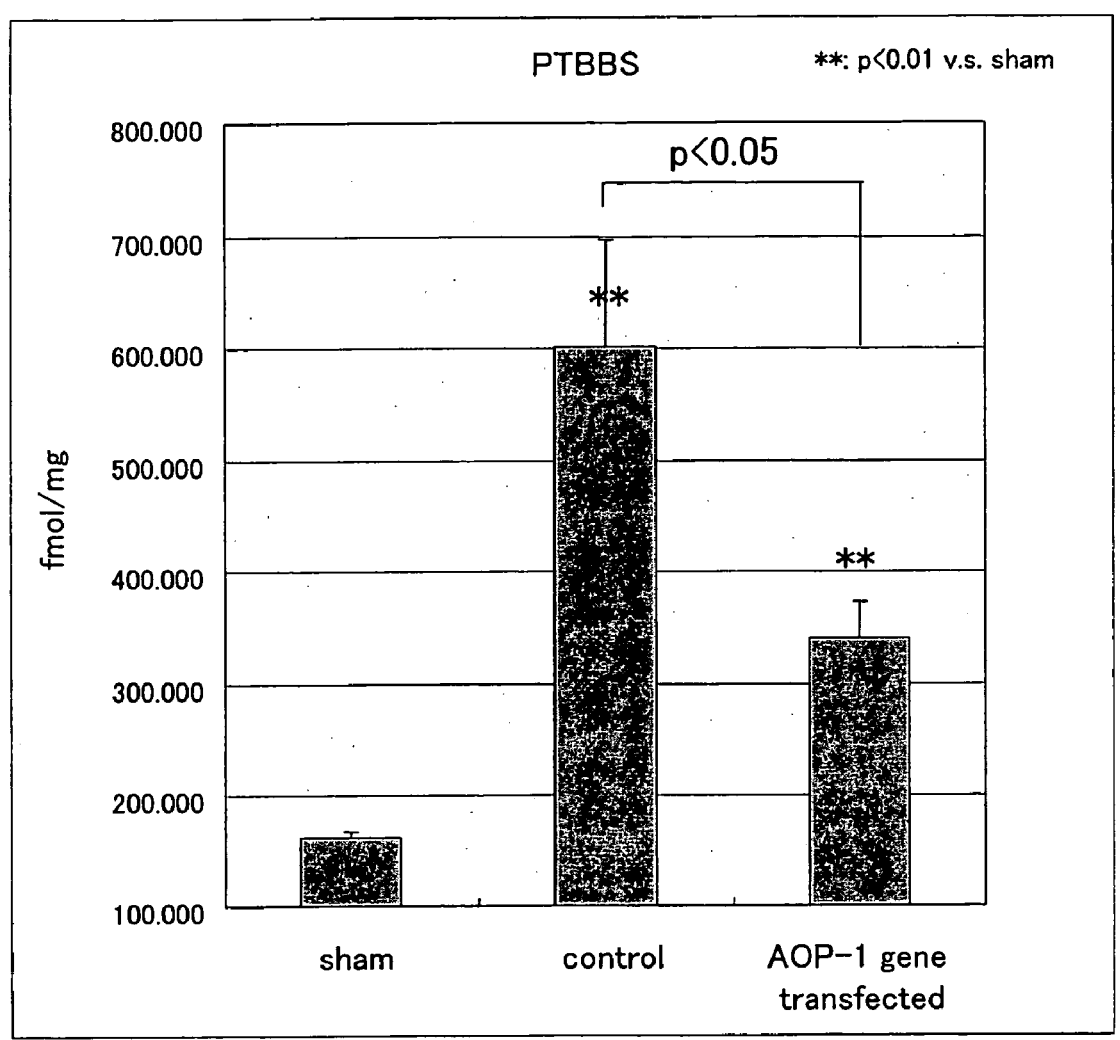
FIG. 14a shows that the PTBBS level was lowered as a result of the protection of neurons by AOP-1.
Figure 14B:
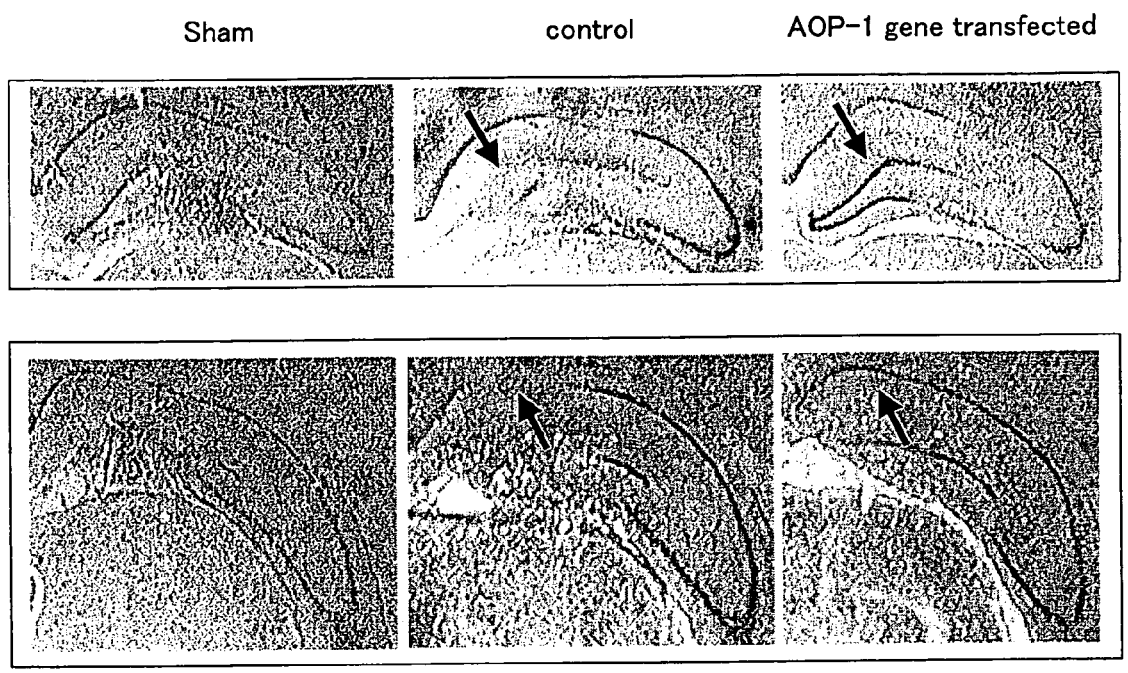
FIG. 14b shows that viable neurons increased as compared with a control as a result of the protection of neurons by AOP-1. The arrows in FIG. 14b indicate injured sites in the control group and the counterparts in the group transfected with AOP-1 gene.

Using the protocol for preparing a brain damage model as described in Example 10-c, $8.5 \times 10^6$ PFU of the modified adenovirus vector for expressing AOP-1 was injected into the brain's hippocampus. After 72 hours, ibotenic acid was injected into the same site in the same manner as described in Example 10-c. A control group transfected with β-galactosidase gene was prepared and also treated with ibotenic acid. After 72 hours, samples for tissue sections were recovered, and after 12 days, samples for analyzing the peripheral benzodiazephine binding site (PTBBS) were recovered. The PTBBS analysis is a quantitative analysis of proliferation/migration of glial cells based on the binding affinity to benzodiazephine. This is a common method for determining the so-called gliosis in which glial cells are activated by neuronal death to migrate/proliferate (Journal of Neuroimmunology 2000 Vol. 1009 105-111, Brain Research 1991 Vol. 565 312-320). The samples for sections were used to prepare sections of 10 μm in thickness by freeze sectioning for Nissl staining as neuron-specific staining. The samples for PTBBS analysis were used by disrupting the hippocampus in a sealed tissue disrupter to prepare a tissue lysate. The protein level was determined by the method described in Example 1-3. The tissue lysate was mixed with tritiated benzodiazephine to perform a binding reaction at 37° C. for 1 hour. Then, the protein with tritiated benzodiazephine bound thereto was trapped in a glass fiber filter and unbound tritiated benzodiazephine was washed off. The radioactivity of the glass fiber filter was assayed. The PTBBS analysis showed that the AOP-1 gene transfected group significantly suppressed the proliferation/migration of glial cells as compared with the control group (β-galactosidase expression group) (FIG. 14a). Neuron-specific staining of tissue sections showed that neurons are qualitatively protected in the AOP-1 gene transfected group as compared with the control group (FIG. 14b). These analyses showed that AOP-1 has the effect of protecting cranial neurons.

Example 18

Protective Effect of AOP-1 on the Kidney

Thy-1 antibody was injected into one kidney isolated from Wister female rats at 7 weeks of age. Immediately after injection of Thy-1 antibody, the adenovirus vector for forced expression of AOP-1 or β-galactosidase was intravenously injected to some animals. Infection of the adenovirus vector was performed at intervals of 1 week for a total of 3 times. After immunization with Thy-1, blood samples were collected on days 3, 7, 14 and 28 and assayed for blood urea nitrogen levels (BUN). After 28 days, tissues were collected and stained with PAS indicative of glycoproteins to give tissue images. One individual in the AOP-1 gene-transfected group was shown by tissue image analysis to have an artificial etiology as compared with other individual findings in Thy-1 nephritis and rejected by a rejection test (Thompson) of the BUN assay on day 7 so that it was excluded from analyses.

Figure 15A:
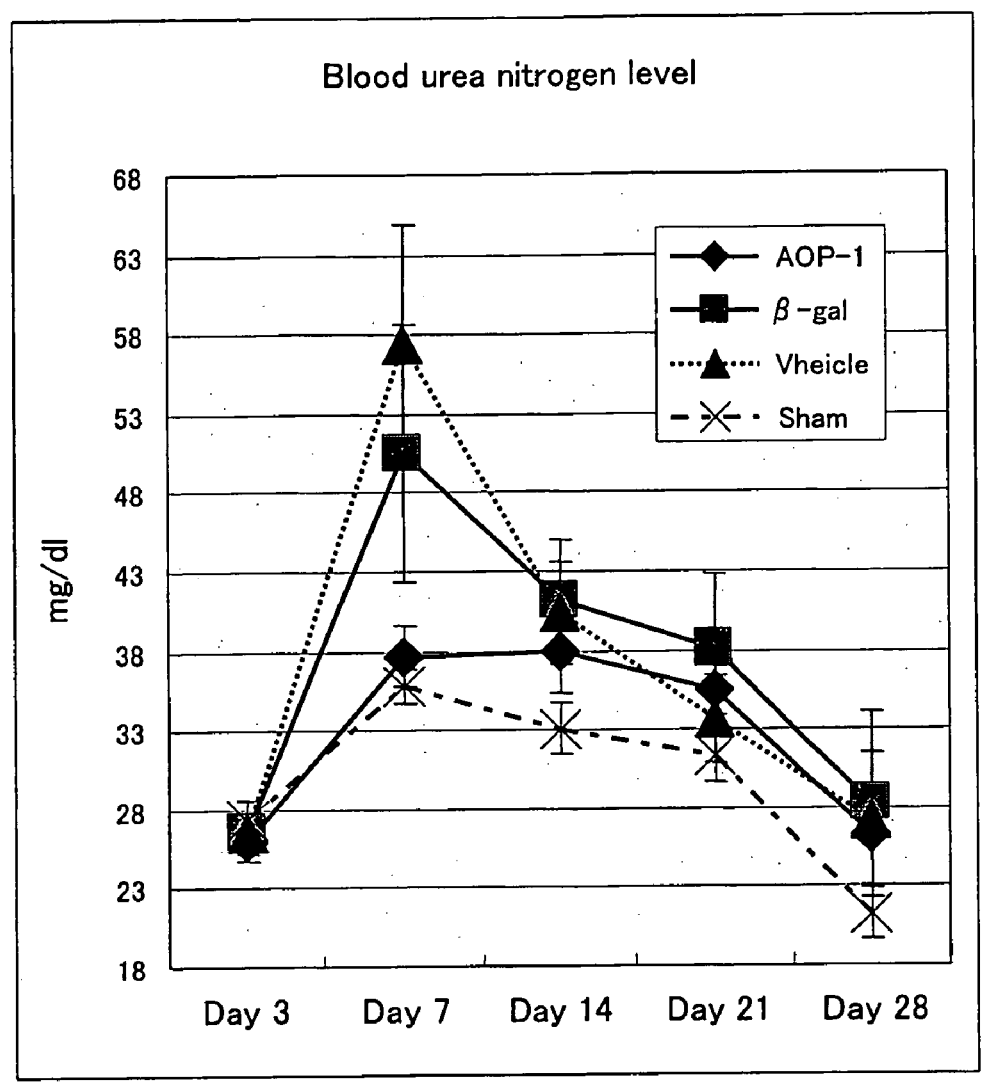
FIG. 15a shows changes in blood urea nitrogen levels with time in various groups.
Figure 15B:
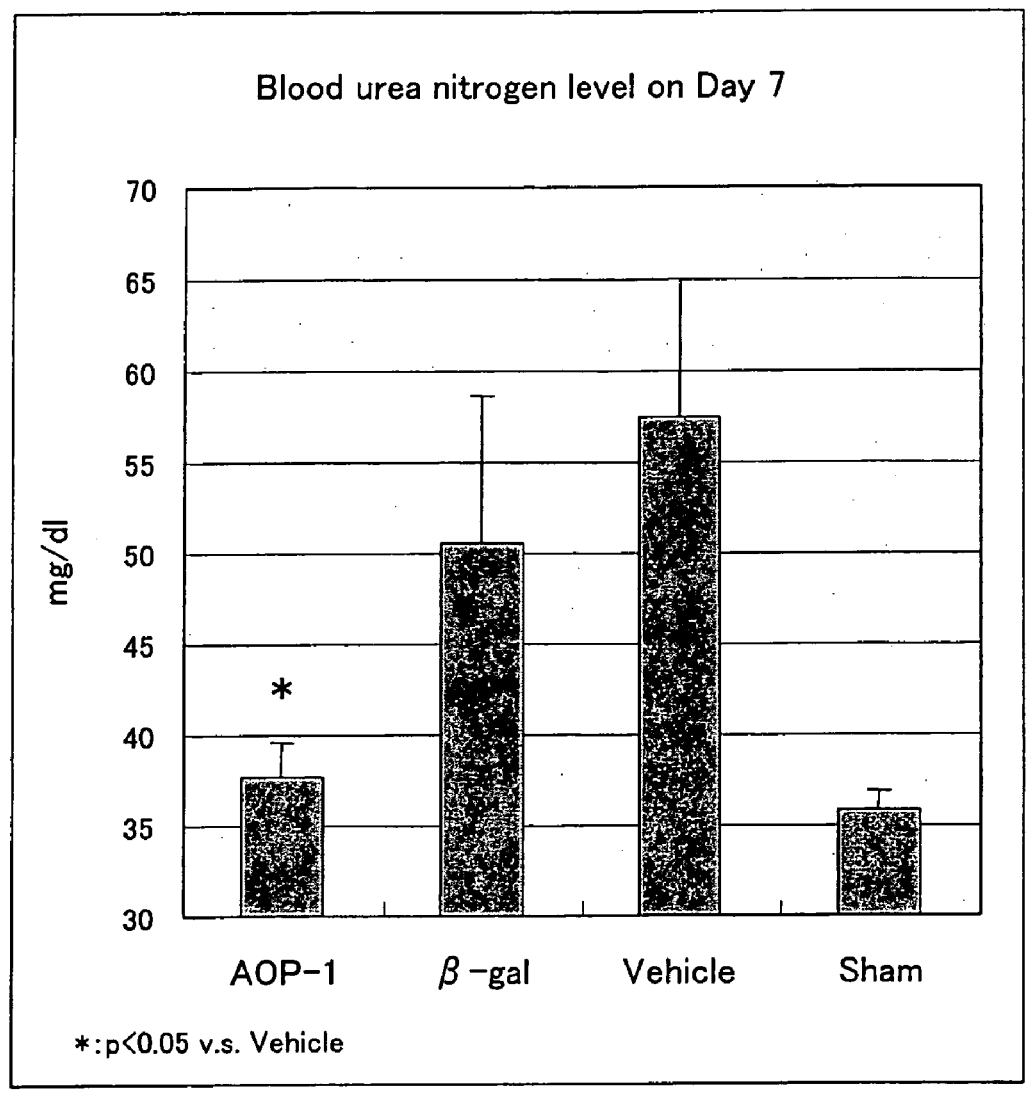
FIG. 15b shows that AOP-1 suppressed the increase of blood urea nitrogen level on day 7 post-inflammation.
Figure 15C:
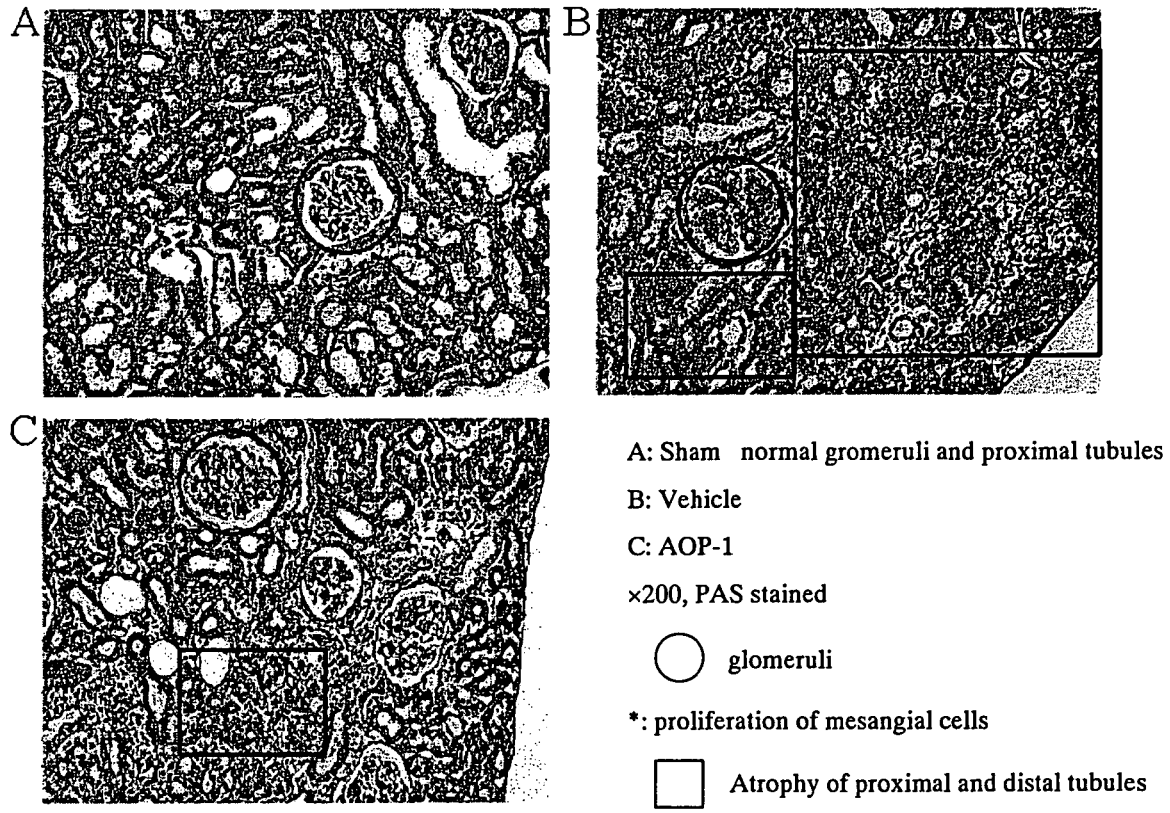
FIG. 15c shows renal tissue images on day 28 post-inflammation to demonstrate that AOP-1 protected renal tubules and glomeruli.
Figure 15C:
Figure 15C:
Figure 15C:
Figure 15C:
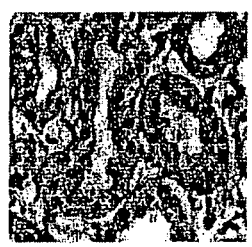
Figure 15C:

FIG. 15a shows changes in BUN levels with time. On day 7, there was a significant difference between the sham group (untransfected group with Thy-1 nephritis not induced) and the vehicle group (untransfected group with Thy-1 nephritis induced), but no significant difference was found between the vehicle group and the sham group at any other instants. The results on day 7 (FIG. 15b) show that the AOP-1 gene transfected group has a significant protective effect as compared with the vehicle group. No significant difference was found between the AOP-1 transfected group and the sham group. FIG. 15c shows typical tissue images. The vehicle group shows widespread atrophy of renal tubules in regions enclosed in boxes with few normal renal tubules, in contrast to the sham group showing no injury. The AOP-1 transfected group also shows atrophy of renal tubules in a region enclosed in a box but to a limited extent as compared with the vehicle group, with an overwhelming majority of renal tubules being normal. Glomeruli are shown in circles. The sham group shows widespread pigmentation (deep purple region marked with asterisk) as compared with the vehicle group. The AOP-1 transfected group shows less pigmentation than the vehicle group. This pigmentation represents proliferation of renal mesangial cells. It has been shown that mesangial cells appear with glomerular injury (Lab. Invest. 1992 Vol. 66 485-497) and that excessive proliferation of mesangial cells induces functional disorder via glomerulosclerosis (Kidney international 1995 Vol. 48 111-117). Thus, the suppressed pigmentation or the suppressed proliferation of mesangial cells seems to result from the protection of renal function by AOP-1. These results demonstrate that AOP-1 has the ability to suppress renal disorder.

The invention claimed is:

1. A method for treating a heart disease, comprising administering by direct injection into a heart an expression vector comprising a nucleic acid sequence encoding AOP-1 operably linked to a promoter, wherein expression of said nucleic acid sequence within cells of the heart enhances the production of AOP-1, and wherein said expression of AOP-1 protects against myocardial cellular death or maintains the heart pulsating function in said heart.

2. The method of claim 1, wherein the heart disease is chronic heart failure, ischemic heart failure or ischemic heart disease.

3. The method of claim 1, wherein said nucleic acid encoding AOP-1 is SEQ ID NO 1.

4. The method of claim 1, wherein said nucleic acid encoding AOP-1 is SEQ ID NO 2.

5. The method of claim 1, wherein said nucleic acid encoding AOP-1 is SEQ ID NO 3.

* * * * *

UNITED STATES PATENT AND TRADEMARK OFFICE
CERTIFICATE OF CORRECTION

PATENT NO.       : 7,598,228 B2                          Page 1 of 1
APPLICATION NO.  : 10/642272
DATED            : October 6, 2009
INVENTOR(S)      : Fumiyuki Hattori et al.

It is certified that error appears in the above-identified patent and that said Letters Patent is hereby corrected as shown below:

On the Title Page, first column, item (63), please change "Feb. 18, 2001" to --Feb. 18, 2002--.

Signed and Sealed this

Thirtieth Day of March, 2010

David J. Kappos
*Director of the United States Patent and Trademark Office*

SEQUENCE LISTING

<160> NUMBER OF SEQ ID NOS: 30

<210> SEQ ID NO 1
<211> LENGTH: 1542
<212> TYPE: DNA
<213> ORGANISM: Homo sapiens

<400> SEQUENCE: 1

```
ctgaagatgg cggctgctgt aggacggttg ctccgagcgt cggttgcccg acatgtgagt      60
gccattcctt gggcatttc tgccactgca gccctcaggc ctgctgcatg tggaagaacg      120
agcttgacaa atttattgtg ttctggttcc agtcaagcaa aattattcag caccagttcc      180
tcatgccatg cacctgctgt cacccagcat gcaccctatt ttaagggtac agccgttgtc      240
aatgagagt tcaaagacct aagccttgat gactttaagg ggaaatattt ggtgcttttc      300
ttctatcctt tggatttcac ctttgtgtgt cctacagaaa ttgttgcttt tagtgacaaa      360
gctaacgaat tcacgatgt gaactgtgaa gttgtcgcag tctcagtgga ttcccacttt      420
agccatcttg cctggataaa tacaccaaga agaatggtg gtttgggcca catgaacatc      480
gcactcttgt cagacttaac taagcagatt cccgagact acggtgtgct gttagaaggt      540
tctggtcttg cactaagagg tctcttcata attgacccca atggagtcat caagcatttg      600
agcgtcaacg atctcccagt gggccgaagc gtggaagaaa ccctccgctt ggtgaaggcg      660
ttccagtatg tagaaacaca tggagaagtc tgcccagcga actggacacc ggattctcct      720
acgatcaagc caagtccagc tgcttccaaa gagtactttc agaaggtaaa tcagtagatc      780
acccatgtgt atctgcacct tctcaactga gagaagaacc acagttgaaa cctgctttta      840
tcattttcaa gatggttatt tgtagaaggc aaggaaccaa ttatgcttgt attcataagt      900
attactctaa atgttttgtt tttgtaattc tggctaggac cttttaaaca tggttagttg      960
ctagtacagg aatcgtttat tggtaacatc ttggtggctg gctagctagt ttctacagaa     1020
cataatttgc ctctatagaa ggctattctt agatcatgtc tcaatggaaa cactcttctt     1080
tcttagcctt acttgaatct tgcctataat aaagtagagc aacacacatt gaaagcttct     1140
gatcaacggt cctgaaattt tcatcttgaa tgtctttgta ttaaactgaa ttttctttta     1200
agctaacaaa gatcataatt ttcaatgatt agccgtgtaa ctcctgcaat gaatgtttat     1260
gtgattgaag caaatgtgaa tcgtattatt ttaaaaagtg gcagagtgac ttaactgatc     1320
atgcatgatc cctcatccct gaaattgagt ttatgtagtc atttactta ttttattcat     1380
tagctaactt tgtctatgta tatttctaga tattgattag tgtaatcgat tataaaggat     1440
atttatcaaa tccagggatt gcattttgaa attataatta ttttctttgc tgaagtattc     1500
attgtaaaac atacaaataa catatttaaa caaaaaaaaa aa                        1542
```

<210> SEQ ID NO 2
<211> LENGTH: 1433
<212> TYPE: DNA
<213> ORGANISM: Rattus norvegicus

<400> SEQUENCE: 2

```
gctatcgtgg ctcttgcgtt ctctgaagat ggcggcagct gcgggaaggt tgctctggtc      60
ctcggtggct cggcctgcga gcactatttt ccggagtatt tctgcctcaa cagttcttag     120
gcctgttgct tctagaagaa cctgcttgac agacatgctg tggtctgcct gtccccaagc     180
aaagtttgcc tttagcacca gttcttcatt ccacacccct gctgtcaccc agcatgcgcc     240
ccatttaaa ggtactgctg ttgtcaatgg agagttcaaa gagctgagtc tcgacgactt     300
taagggaa tacttggtgc ttttcttcta cccctttgga ttcacatttg tgtgtcctac     360
agaaattgtt gctttcagtg acaaagccaa tgagtttcat gacgtaaact gtgaagtagt     420
tgcggtttct gtggattccc acttcagtca tcttgcctgg atcaacacgc caagaaagaa     480
tggtggtttg ggccacatga acatcacgct gttgtcggac ttaactaagc agatatcccg     540
```

```
agactacgga gtactgttgg aaagtgctgg cattgcgctc agaggtctct tcattattga    600
ccctaatggt gtcatcaagc acctgagtgt caatgacctt ccggtgggcc gaagtgtgga    660
agaaccactc cgtttggtaa aggcgttcca gtttgtggag acccatggag aagtctgccc    720
acccaactgg acaccagagt cccctacgat caagccaagt ccaacagctt caaaagagta    780
ctttgagaag gtccatcaat aataggtcat cctatgtctg ctggtttacc tgaagcttct    840
catgccaaaa gagagcccca gctggaatcc tgaagattat ttatagaatg caaaaacct     900 caccatgctt gtgtttataa gtactgctcc atgggctttg taattttaag acaggttcag    960
gttaaaggtg gccagctcct tccatagctg tccttactag ggacttcttg atggctacca   1020
attctctaca gtgcttggt ccccatttct tagatcatgt cttcagaggg ttaagatttc    1080
ttagcctgcc ctgaagcttg gtctacagtg aagtagcaca tagcaccagt acttagtgaa   1140
atgaagtagc acatagcgcc agcacttagt gaaatgaag agcatatagt gccagcactt    1200
agtgaaagct tctgatcaag gtcctgaaat ttcctcttgg atttttgtta attatgctga   1260
atttcccatt attttttagt gtagtcatta actcacagtg tccttgtgtg ttctaaggta   1320
ttgatgagtt ataatcatga aggactatgt ttctaaaaca ctatgtcatt ttcttttctt   1380
caagtgctgg atgtaaagaa taaaataaa cattaagata aaaaaaaaaa aaa            1433

<210> SEQ ID NO 3
<211> LENGTH: 1382
<212> TYPE: DNA
<213> ORGANISM: Mus sp.

<400> SEQUENCE: 3
ctactcctcg gtatctccgc ctatcgtgcc tcttgcgtgc tctgaagatg gcggcagctg     60
cgggaaggtt gctctggtcc tcggttgctc gtcatgcaag tgctatttcc cggagtattt    120
ctgcctcaac agttcttagg cctgttgctt ctagaagaac ctgtttgaca gacatactgt    180
ggtctgcctc tgcccaagga agtcagcct ttagcaccag ttcctctttc cacacccctg     240
ctgtcaccca gcacgcgccc tattttaaag gtactgctgt tgtcaatgga gagttcaaag    300
agctgagtct cgacgacttt aagggaaaat acttggtgct tttcttctac cctttggatt    360
tcacatttgt gtgtcctaca gaaattgttg ctttcagtga caaagccaat gaatttcatg    420
atgtaaactg tgaagtagtt gcagtttcag tggattccca cttcagtcat cttgcctgga    480
tcaacacacc aagaaagaat ggtggtttgg gccacatgaa catcacactg ttgtcggata    540
taactaagca gatatcccga gactacggag tgctgttgga aagtgctggc attgcactca    600
gaggtctctt cattattgac cctaatggtg tcgtcaagca cctgagtgtc aacgaccttc    660
cggtgggccg cagtgtggaa gaaacactcc gtttggtaaa ggcgttccag tttgtagaga    720
cccatggaga agtctgccca gccaactgga caccagagtc ccctacgatc aagccaagtc    780
caacagcttc aaagagtac tttgagaagg tccatcagta ggccatccta tgtctgcaat     840
tacctgaagc ttttcaggcc aaaaagagc cccagctgga atccttccaa tgccttgaag    900
attatttata gaatggcaaa acctcattat gtttgtgttt ataagtactg ctccacaggc    960
tttgtaattc taagacaggt tcaggctctc taaaggtggc tagctgcttc catagctgcc   1020
cttactaggg acttcttggt ggctaaccaa ttctccccga gtgctttgcc cccatttctt   1080
ggatcatgtc cttagagggt aagcattctt tcccttagcc tgccctgaac cttggtctac   1140
agtgaagtag cacatagtgc cagtacttgg tgaaatgaag tagcacatag caccagcact   1200
```

```
taatggaagc ttctgatcaa ggtcctaaaa tttcctcttg aatttttgtg aattatgctg    1260
aatttcccct tttttttttt taaacagtgt ccttgtgtgt tctgaggtat tgaagaggta    1320
taatcatgaa ggactatgtc taatccataa gtcattttct tcaagagctg gatatataga    1380
at                                                                   1382
```

<210> SEQ ID NO 4
<211> LENGTH: 256
<212> TYPE: PRT
<213> ORGANISM: Homo sapiens

<400> SEQUENCE: 4

```
Met Ala Ala Val Gly Arg Leu Leu Arg Ala Ser Val Ala Arg His
1               5                   10                  15

Val Ser Ala Ile Pro Trp Gly Ile Ser Ala Thr Ala Ala Leu Arg Pro
            20                  25                  30

Ala Ala Cys Gly Arg Thr Ser Leu Thr Asn Leu Leu Cys Ser Gly Ser
        35                  40                  45

Ser Gln Ala Lys Leu Phe Ser Thr Ser Ser Cys His Ala Pro Ala
    50                  55                  60

Val Thr Gln His Ala Pro Tyr Phe Lys Gly Thr Ala Val Val Asn Gly
65                  70                  75                  80

Glu Phe Lys Asp Leu Ser Leu Asp Asp Phe Lys Gly Lys Tyr Leu Val
                85                  90                  95

Leu Phe Phe Tyr Pro Leu Asp Phe Thr Phe Val Cys Pro Thr Glu Ile
            100                 105                 110

Val Ala Phe Ser Asp Lys Ala Asn Glu Phe His Asp Val Asn Cys Glu
        115                 120                 125

Val Val Ala Val Ser Val Asp Ser His Phe Ser His Leu Ala Trp Ile
    130                 135                 140

Asn Thr Pro Arg Lys Asn Gly Gly Leu Gly His Met Asn Ile Ala Leu
145                 150                 155                 160

Leu Ser Asp Leu Thr Lys Gln Ile Ser Arg Asp Tyr Gly Val Leu Leu
                165                 170                 175

Glu Gly Ser Gly Leu Ala Leu Arg Gly Leu Phe Ile Ile Asp Pro Asn
            180                 185                 190

Gly Val Ile Lys His Leu Ser Val Asn Asp Leu Pro Val Gly Arg Ser
        195                 200                 205

Val Glu Glu Thr Leu Arg Leu Val Lys Ala Phe Gln Tyr Val Glu Thr
    210                 215                 220

His Gly Glu Val Cys Pro Ala Asn Trp Thr Pro Asp Ser Pro Thr Ile
225                 230                 235                 240

Lys Pro Ser Pro Ala Ala Ser Lys Glu Tyr Phe Gln Lys Val Asn Gln
                245                 250                 255
```

<210> SEQ ID NO 5
<211> LENGTH: 257
<212> TYPE: PRT
<213> ORGANISM: Rattus norvegicus

<400> SEQUENCE: 5

```
Met Ala Ala Ala Gly Arg Leu Leu Trp Ser Ser Val Ala Arg Pro
1               5                   10                  15

Ala Ser Thr Ile Phe Arg Ser Ile Ser Ala Ser Thr Val Leu Arg Pro
            20                  25                  30

Val Ala Ser Arg Arg Thr Cys Leu Thr Asp Met Leu Trp Ser Ala Cys
```

```
                35                  40                  45
Pro Gln Ala Lys Phe Ala Phe Ser Thr Ser Ser Ser Phe His Thr Pro
         50                  55                  60
Ala Val Thr Gln His Ala Pro His Phe Lys Gly Thr Ala Val Val Asn
 65                  70                  75                  80
Gly Glu Phe Lys Glu Leu Ser Leu Asp Asp Phe Lys Gly Lys Tyr Leu
                 85                  90                  95
Val Leu Phe Phe Tyr Pro Leu Asp Phe Thr Phe Val Cys Pro Thr Glu
                100                 105                 110
Ile Val Ala Phe Ser Asp Lys Ala Asn Glu Phe His Asp Val Asn Cys
            115                 120                 125
Glu Val Val Ala Val Ser Val Asp Ser His Phe Ser His Leu Ala Trp
130                 135                 140
Ile Asn Thr Pro Ala Lys Asn Gly Gly Leu Gly His Met Asn Ile Thr
145                 150                 155                 160
Leu Leu Ser Asp Leu Thr Lys Gln Ile Ser Arg Asp Tyr Gly Val Leu
                165                 170                 175
Leu Glu Ser Ala Gly Ile Ala Leu Arg Gly Leu Phe Ile Ile Asp Pro
            180                 185                 190
Asn Gly Val Ile Lys His Leu Ser Val Asn Asp Leu Pro Val Gly Arg
        195                 200                 205
Ser Val Glu Glu Pro Leu Arg Leu Val Lys Ala Phe Gln Phe Val Glu
    210                 215                 220
Thr His Gly Glu Val Cys Pro Pro Asn Trp Thr Pro Glu Ser Pro Thr
225                 230                 235                 240
Ile Lys Pro Ser Pro Thr Ala Ser Lys Glu Tyr Phe Glu Lys Val His
                245                 250                 255
Gln

<210> SEQ ID NO 6
<211> LENGTH: 257
<212> TYPE: PRT
<213> ORGANISM: Mus sp.

<400> SEQUENCE: 6

Met Ala Ala Ala Gly Arg Leu Leu Trp Ser Ser Val Ala Arg His
  1               5                  10                  15
Ala Ser Ala Ile Ser Arg Ser Ile Ser Ala Ser Thr Val Leu Arg Pro
             20                  25                  30
Val Ala Ser Arg Arg Thr Cys Leu Thr Asp Ile Leu Trp Ser Ala Ser
         35                  40                  45
Ala Gln Gly Leu Ser Ala Phe Ser Thr Ser Ser Phe His Thr Pro
         50                  55                  60
Ala Val Thr Gln His Ala Pro Tyr Phe Lys Gly Thr Ala Val Val Asn
 65                  70                  75                  80
Gly Glu Phe Lys Glu Leu Ser Leu Asp Asp Phe Lys Gly Lys Tyr Leu
                 85                  90                  95
Val Leu Phe Phe Tyr Pro Leu Asp Phe Thr Phe Val Cys Pro Thr Glu
                100                 105                 110
Ile Val Ala Phe Ser Asp Lys Ala Asn Glu Phe His Asp Val Asn Cys
            115                 120                 125
Glu Val Val Ala Val Ser Val Asp Ser His Phe Ser His Leu Ala Trp
130                 135                 140
Ile Asn Thr Pro Arg Lys Asn Gly Gly Leu Gly His Met Asn Ile Thr
```

```
145                 150                 155                 160
Leu Leu Ser Asp Ile Thr Lys Gln Ile Ser Arg Asp Tyr Gly Val Leu
                165                 170                 175
Leu Glu Ser Ala Gly Ile Ala Leu Arg Gly Leu Phe Ile Ile Asp Pro
            180                 185                 190
Asn Gly Val Val Lys His Leu Ser Val Asn Asp Leu Pro Val Gly Arg
        195                 200                 205
Ser Val Glu Glu Thr Leu Arg Leu Val Lys Ala Phe Gln Phe Val Glu
    210                 215                 220
Thr His Gly Glu Val Cys Pro Ala Asn Trp Thr Pro Glu Ser Pro Thr
225                 230                 235                 240
Ile Lys Pro Ser Pro Thr Ala Ser Lys Glu Tyr Phe Glu Lys Val His
                245                 250                 255
Gln
```

<210> SEQ ID NO 7
<211> LENGTH: 21
<212> TYPE: DNA
<213> ORGANISM: Artificial Sequence
<220> FEATURE:
<223> OTHER INFORMATION: Forward Primer

<400> SEQUENCE: 7
tgcagtttca gtggattccc a                                              21

<210> SEQ ID NO 8
<211> LENGTH: 18
<212> TYPE: DNA
<213> ORGANISM: Artificial Sequence
<220> FEATURE:
<223> OTHER INFORMATION: Reverse Primer

<400> SEQUENCE: 8
ttcatgtggc ccaaacca                                                  18

<210> SEQ ID NO 9
<211> LENGTH: 28
<212> TYPE: DNA
<213> ORGANISM: Artificial Sequence
<220> FEATURE:
<223> OTHER INFORMATION: Probe

<400> SEQUENCE: 9
tcttgcctgg atcaacacac caagaaag                                       28

<210> SEQ ID NO 10
<211> LENGTH: 22
<212> TYPE: DNA
<213> ORGANISM: Artificial Sequence
<220> FEATURE:
<223> OTHER INFORMATION: Forward Primer

<400> SEQUENCE: 10
ccctctgctt gctgatgtga ct                                             22

<210> SEQ ID NO 11
<211> LENGTH: 20
<212> TYPE: DNA
<213> ORGANISM: Artificial Sequence
<220> FEATURE:
<223> OTHER INFORMATION: Reverse Primer

<400> SEQUENCE: 11

-continued cctgtaagcg atgccctcat                                                   20

<210> SEQ ID NO 12
<211> LENGTH: 29
<212> TYPE: DNA
<213> ORGANISM: Artificial Sequence
<220> FEATURE:
<223> OTHER INFORMATION: Probe

<400> SEQUENCE: 12
agcttgtccc agaattacgg cgtgttgaa                                         29

<210> SEQ ID NO 13
<211> LENGTH: 19
<212> TYPE: DNA
<213> ORGANISM: Artificial Sequence
<220> FEATURE:
<223> OTHER INFORMATION: Forward Primer

<400> SEQUENCE: 13
gcggatgaag agaggcatg                                                    19

<210> SEQ ID NO 14
<211> LENGTH: 18
<212> TYPE: DNA
<213> ORGANISM: Artificial Sequence
<220> FEATURE:
<223> OTHER INFORMATION: Reverse Primer

<400> SEQUENCE: 14
gccacaccgt cctttcca                                                     18

<210> SEQ ID NO 15
<211> LENGTH: 23
<212> TYPE: DNA
<213> ORGANISM: Artificial Sequence
<220> FEATURE:
<223> OTHER INFORMATION: Probe

<400> SEQUENCE: 15
tggagacctg ggcaatgtgg ctg                                               23

<210> SEQ ID NO 16
<211> LENGTH: 17
<212> TYPE: DNA
<213> ORGANISM: Artificial Sequence
<220> FEATURE:
<223> OTHER INFORMATION: Forward Primer

<400> SEQUENCE: 16
acgggtgctc agcctcc                                                      17

<210> SEQ ID NO 17
<211> LENGTH: 18
<212> TYPE: DNA
<213> ORGANISM: Artificial Sequence
<220> FEATURE:
<223> OTHER INFORMATION: Reverse Primer

<400> SEQUENCE: 17
aggcttgtgc cctgcttc                                                     18

<210> SEQ ID NO 18
<211> LENGTH: 25
<212> TYPE: DNA

```
<213> ORGANISM: Artificial Sequence
<220> FEATURE:
<223> OTHER INFORMATION: Probe

<400> SEQUENCE: 18
cagcctgcac tgaggagatc cctca                                             25

<210> SEQ ID NO 19
<211> LENGTH: 28
<212> TYPE: DNA
<213> ORGANISM: Artificial Sequence
<220> FEATURE:
<223> OTHER INFORMATION: Forward Primer

<400> SEQUENCE: 19
aaccgcggtc gtggctcttg cgttctct                                          28

<210> SEQ ID NO 20
<211> LENGTH: 30
<212> TYPE: DNA
<213> ORGANISM: Artificial Sequence
<220> FEATURE:
<223> OTHER INFORMATION: Reverse Primer

<400> SEQUENCE: 20
gcgctagctt attgatggac cttctcaaag                                        30

<210> SEQ ID NO 21
<211> LENGTH: 20
<212> TYPE: DNA
<213> ORGANISM: Artificial Sequence
<220> FEATURE:
<223> OTHER INFORMATION: Forward Primer

<400> SEQUENCE: 21
ttacagattg ccgcctgctc                                                   20

<210> SEQ ID NO 22
<211> LENGTH: 20
<212> TYPE: DNA
<213> ORGANISM: Artificial Sequence
<220> FEATURE:
<223> OTHER INFORMATION: Reverse Primer

<400> SEQUENCE: 22
ccagcagtgg aataaggcct                                                   20

<210> SEQ ID NO 23
<211> LENGTH: 25
<212> TYPE: DNA
<213> ORGANISM: Artificial Sequence
<220> FEATURE:
<223> OTHER INFORMATION: Probe

<400> SEQUENCE: 23
aatcacgacc cactgcaagg aacca                                             25

<210> SEQ ID NO 24
<211> LENGTH: 19
<212> TYPE: DNA
<213> ORGANISM: Artificial Sequence
<220> FEATURE:
<223> OTHER INFORMATION: Forward Primer

<400> SEQUENCE: 24
tgcaccacca actgcttag                                                    19
```

<210> SEQ ID NO 25
<211> LENGTH: 19
<212> TYPE: DNA
<213> ORGANISM: Artificial Sequence
<220> FEATURE:
<223> OTHER INFORMATION: Reverse Primer

<400> SEQUENCE: 25
ggatgcaggg atgatgttc                                                19

<210> SEQ ID NO 26
<211> LENGTH: 23
<212> TYPE: DNA
<213> ORGANISM: Artificial Sequence
<220> FEATURE:
<223> OTHER INFORMATION: Probe

<400> SEQUENCE: 26
cagaagactg tggatggccc ctc                                           23

<210> SEQ ID NO 27
<211> LENGTH: 877
<212> TYPE: DNA
<213> ORGANISM: Rattus norvegicus

<400> SEQUENCE: 27
gaattcggca cgagggtcgt ccgcgtgtcc ggctcttgcc cacgcagtca tggcctccgg    60
caacgcgcac atcggaaagc ctgcccctga cttcacgggc accgccgtgg tggatggtgc   120
ctttaaggaa atcaagcttt cagactacag agggaagtac gtggtcctct ttttctatcc   180
actggacttc acttttgttt gccccacgga gatcatcgct tttagcgacc acgctgagga   240
cttccgaaag ctaggctgcg aggtgctggg agtgtctgtg actctcagt tcacccacct    300 ggcctggatc aataccccac ggaaggaggg aggcttgggc ccactgaata tccctctgct   360
tgctgatgtg actaaaagct tgtcccagaa ttacggcgtg ttgaaaaatg atgagggcat   420
cgcttacagg ggcctcttta tcatcgatgc caagggtgtc cttcgccaga tcacagtcaa   480
cgacctacct gtgggacgct ctgtagatga ggctctccgc ctcgtccagg cctttcagta   540
tacagatgag catggggaag tctgtcctgc tggctggaag cccggcagtg acaccatcaa   600
acccaatgtg gatgacagca aggaatactt ctccaaacac aactgagatg ggtaaacatc   660
ggtgagcctg aatcccggat ctcacctgcg cccttacctg gatgtcctgt gctggcccag   720
aaaacgctag atcttcctct acattctaaa ggggctggag gctaggccga ggctttctca   780
ttacccacct ggaatctggt gaatagtgac cctgccctga gcacacccag ctgggcccag   840
gtctatagga aaccaataaa gtattaggga cagtgta                            877

<210> SEQ ID NO 28
<211> LENGTH: 198
<212> TYPE: PRT
<213> ORGANISM: Rattus norvegicus

<400> SEQUENCE: 28

Met Ala Ser Gly Asn Ala His Ile Gly Lys Pro Ala Pro Asp Phe Thr
1               5                   10                  15

Gly Thr Ala Val Val Asp Gly Ala Phe Lys Glu Ile Lys Leu Ser Asp
            20                  25                  30

Tyr Arg Gly Lys Tyr Val Val Leu Phe Phe Tyr Pro Leu Asp Phe Thr
        35                  40                  45

```
Phe Val Cys Pro Thr Glu Ile Ile Ala Phe Ser Asp His Ala Glu Asp
         50                  55                  60

Phe Arg Lys Leu Gly Cys Glu Val Leu Gly Val Ser Val Asp Ser Gln
 65                  70                  75                  80

Phe Thr His Leu Ala Trp Ile Asn Thr Pro Arg Lys Glu Gly Gly Leu
                 85                  90                  95

Gly Pro Leu Asn Ile Pro Leu Leu Ala Asp Val Thr Lys Ser Leu Ser
            100                 105                 110

Gln Asn Tyr Gly Val Leu Lys Asn Asp Glu Gly Ile Ala Tyr Arg Gly
            115                 120                 125

Leu Phe Ile Ile Asp Ala Lys Gly Val Leu Arg Gln Ile Thr Val Asn
130                 135                 140

Asp Leu Pro Val Gly Arg Ser Val Asp Glu Ala Leu Arg Leu Val Gln
145                 150                 155                 160

Ala Phe Gln Tyr Thr Asp Glu His Gly Glu Val Cys Pro Ala Gly Trp
                165                 170                 175

Lys Pro Gly Ser Asp Thr Ile Lys Pro Asn Val Asp Asp Ser Lys Glu
            180                 185                 190

Tyr Phe Ser Lys His Asn
            195

<210> SEQ ID NO 29
<211> LENGTH: 560
<212> TYPE: DNA
<213> ORGANISM: Homo sapiens

<400> SEQUENCE: 29
atggcgacga aggccgtgtg cgtgctgaag ggcgacggcc cagtgcaggg catcatcaat      60
ttcgagcaga aggaaagtaa tggaccagtg aaggtgtggg gaagcattaa aggactgact     120
gaaggcctgc atggattcca tgttcatgag tttggagata tacggcaggc tgtaccagtt     180
gcaggtcctc actttaatcc tctatccaga aaacacggtg gccaaaggat gaagagagg      240
catgttggag acttgggcaa tgtgactgct gacaaagatg gtgtggccga tgtgtctatt     300
gaagattctg tgatctcact ctcaggagac cattgcatca ttggccgcac actggtggtc     360
catgaaaaag cagatgactt gggcaaaggt ggaaatgaag aaagtacaaa gacaggaaac     420
gctggaagtc gtttggcttg tggtgtaatt gggatcgccc aataaacatt cccttggatg     480
tagtctgagg cccttaact catctgttat cctgctagct gtagaaatgt atcctgataa      540
acattaaaca ctgtaatctt                                                 560

<210> SEQ ID NO 30
<211> LENGTH: 154
<212> TYPE: PRT
<213> ORGANISM: Homo sapiens

<400> SEQUENCE: 30

Met Ala Thr Lys Ala Val Cys Val Leu Lys Gly Asp Gly Pro Val Gln
  1               5                  10                  15

Gly Ile Ile Asn Phe Glu Gln Lys Glu Ser Asn Gly Pro Val Lys Val
             20                  25                  30

Trp Gly Ser Ile Lys Gly Leu Thr Glu Gly Leu His Gly Phe His Val
         35                  40                  45

His Glu Phe Gly Asp Asn Thr Ala Gly Cys Thr Ser Ala Gly Pro His
     50                  55                  60
```

-continued

```
Phe Asn Pro Leu Ser Arg Lys His Gly Gly Pro Lys Asp Glu Glu Arg
 65                  70                  75                  80

His Val Gly Asp Leu Gly Asn Val Thr Ala Asp Lys Asp Gly Val Ala
                 85                  90                  95

Asp Val Ser Ile Glu Asp Ser Val Ile Ser Leu Ser Gly Asp His Cys
            100                 105                 110

Ile Ile Gly Arg Thr Leu Val Val His Glu Lys Ala Asp Asp Leu Gly
        115                 120                 125

Lys Gly Gly Asn Glu Glu Ser Thr Lys Thr Gly Asn Ala Gly Ser Arg
    130                 135                 140

Leu Ala Cys Gly Val Ile Gly Ile Ala Gln
145                 150
```